(12) United States Patent
Vacca et al.

(10) Patent No.: US 8,253,938 B2
(45) Date of Patent: Aug. 28, 2012

(54) METHOD AND APPARATUS FOR RAPIDLY COUNTING AND IDENTIFYING BIOLOGICAL PARTICLES IN A FLOW STREAM

(75) Inventors: Giacomo Vacca, San Jose, CA (US); Norman R. Goldblatt, Mountain View, CA (US); Michael W. Yee, Mount Shasta, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/116,594

(22) Filed: May 26, 2011

(65) Prior Publication Data

US 2011/0228271 A1    Sep. 22, 2011

Related U.S. Application Data

(60) Continuation of application No. 12/880,523, filed on Sep. 13, 2010, now Pat. No. 8,045,162, which is a division of application No. 11/934,277, filed on Nov. 2, 2007, now Pat. No. 7,804,594.

(60) Provisional application No. 60/877,874, filed on Dec. 29, 2006.

(51) Int. Cl.
   *G01N 21/00* (2006.01)
(52) U.S. Cl. ......................... 356/337; 356/338
(58) Field of Classification Search .......... 356/336–343, 356/317–318, 39, 72–73, 23–26, 441–442; 382/133; 250/461.2, 573–575, 564–565; 422/73; 436/63
   See application file for complete search history.

(56) References Cited

U.S. PATENT DOCUMENTS

| | | | |
|---|---|---|---|
| 4,579,136 A | 4/1986 | Oman et al. |
| 4,920,275 A | 4/1990 | Itoh |
| 4,999,513 A | 3/1991 | Ito et al. |
| 5,017,497 A | 5/1991 | de Grooth et al. |
| 5,072,382 A | 12/1991 | Kamentsky |
| 5,083,014 A | 1/1992 | Kosaka |
| 5,125,737 A | 6/1992 | Rodriguez et al. |
| 5,138,181 A | 8/1992 | Lefevre et al. |

(Continued)

FOREIGN PATENT DOCUMENTS

DE    4309328 A1    9/1994

(Continued)

OTHER PUBLICATIONS

Cell-Dyn Sapphire RTM. [online] 2007 [retrieved on Nov. 25, 2007]. Retrieved from the Internet:<http://www.abbottdignostics.com/Products/Instruments.sub.—by.sub.—Platform/default.cfm?system=CELL-DYN&suffix=Sapphire>>.

(Continued)

*Primary Examiner* — Tri T Ton
(74) *Attorney, Agent, or Firm* — Peter A. Socarras; Bozicevic, Field & Francis LLP

(57) ABSTRACT

A method for increasing the throughput, or the precision, or both the precision and the throughput, of a flow cytometer, or of a hematology analyzer employing a flow cytometer, by utilizing the technique of laser rastering. Laser rastering involves sweeping a laser beam across a flowing sample stream in a hematology analyzer. An apparatus suitable for carrying out the method of this invention comprises an optical module comprising a source of light, a scanning device, a lens or system of lenses, a flow cell, detectors, and filters; and an electronic module comprising preamplifiers, analog signal conditioning elements, analog-to-digital converters, field-programmable gate arrays, digital signal processing elements, and data storage elements.

20 Claims, 21 Drawing Sheets

U.S. PATENT DOCUMENTS

| | | | |
|---|---|---|---|
| 5,242,792 | A | 9/1993 | Rudolph et al. |
| 5,350,695 | A | 9/1994 | Colella et al. |
| 5,426,499 | A | 6/1995 | Kosaka et al. |
| 5,444,527 | A | 8/1995 | Kosaka |
| 5,469,251 | A | 11/1995 | Kosaka et al. |
| 5,521,699 | A | 5/1996 | Kosaka et al. |
| 5,523,207 | A | 6/1996 | Kamentsky et al. |
| 5,548,395 | A | 8/1996 | Kosaka |
| 5,644,388 | A | 7/1997 | Maekawa et al. |
| 5,812,419 | A | 9/1998 | Chupp et al. |
| 5,824,269 | A | 10/1998 | Kosaka et al. |
| 5,939,326 | A | 8/1999 | Chupp et al. |
| 5,962,238 | A | 10/1999 | Sizto et al. |
| 6,002,788 | A | 12/1999 | Luther |
| 6,524,858 | B1 | 2/2003 | Zelmanovic et al. |
| 6,579,685 | B1 | 6/2003 | Russell et al. |
| 6,603,537 | B1 | 8/2003 | Dietz et al. |
| 6,618,143 | B2 | 9/2003 | Roche et al. |
| 6,619,050 | B2 | 9/2003 | Hozumi et al. |
| 6,671,044 | B2 | 12/2003 | Ortyn et al. |
| 6,687,395 | B1 | 2/2004 | Dietz et al. |
| 6,975,400 | B2 | 12/2005 | Ortyn et al. |
| 7,344,890 | B2 | 3/2008 | Perez et al. |
| 2002/0057432 | A1 | 5/2002 | Ortyn et al. |
| 2002/0146734 | A1 | 10/2002 | Ortyn et al. |
| 2003/0100024 | A1 | 5/2003 | Cassells et al. |
| 2003/0143117 | A1 | 7/2003 | Nagai et al. |
| 2005/0280817 | A1 | 12/2005 | Horchner et al. |

FOREIGN PATENT DOCUMENTS

| | | | |
|---|---|---|---|
| EP | 501005 | A2 | 9/1992 |
| EP | 681178 | B1 | 7/2001 |
| EP | 1376135 | A2 | 1/2004 |
| JP | 1270644 | A2 | 10/1989 |
| JP | 2105041 | A2 | 4/1990 |
| JP | 3150444 | A2 | 6/1991 |
| JP | 3154850 | A2 | 7/1991 |
| WO | WO9014589 | A1 | 11/1990 |
| WO | WO03023368 | A1 | 3/2003 |
| WO | WO2006104699 | A1 | 10/2006 |

OTHER PUBLICATIONS

Cell-Dyn Ruby RTM. [online] 2007 [retrieved on Nov. 25, 2007]. Retrieved from the Internet:<http://www.abbottdiagnostics.com/Products/Instruments.sub.—by.sub.—Plat—form/default.cfm?sys.sub.—id=158 >>.

European Patent Office, International Search Report, May 20, 2008.

Innovadyne Technologies., Inc., pipetting solutions at Innovadyne Technologies, [online], [retrieved on Apr. 30, 2009]. Retrieved from the Internet: (URL:(http://www.innovadyne.com/_pipetting.html ), 1-3.

Liu, et al., "Bubble-induced acoustic micromixing", Lab Chip, 2008, 2, 151-157.

Patterson., Dispensing Precision and Accuracy for the JANUS Varispan Automated Workstation using Versa Tip, © PerkinElmer, Inc.,2007, 1-4.

PCT, Notification of Transmittal of the International Search Report and the Written Opinion of the International Searching Authority, or the Declaration, Date of Mailing Feb. 20, 2009.

University of California, Berkeley. Cancer Research Laboratory. CRL Facilities, Flow Cytometry Principles [online], [retrieved on Mar. 30, 2006]. Retrieved from the Internet: (URL: http://biology.berkeley.edu/crl/ flow_cytometry_basic.html), 1-6.

Vortex mixer—Wikipedia, the free encyclopedia [online], [retrieved on Apr. 30, 2009]. Retrieved from the Internet: (URL: http://en.wikipedia.org/wiki/Vortex_mixer ), 1-2.

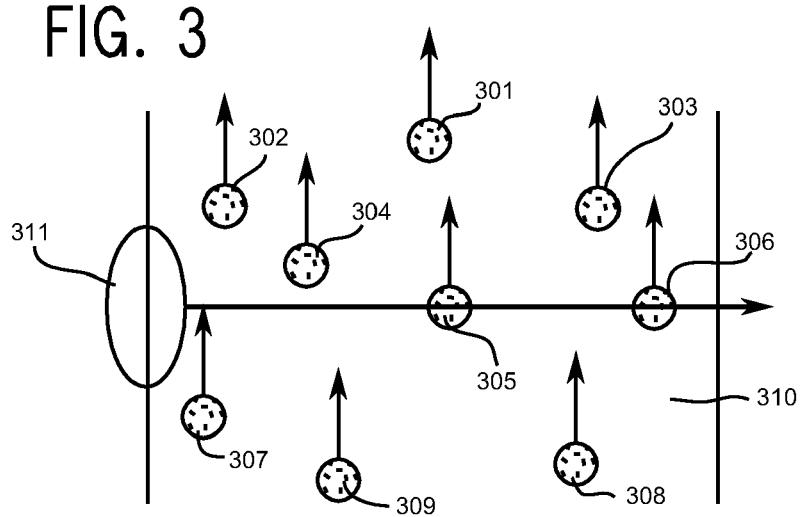
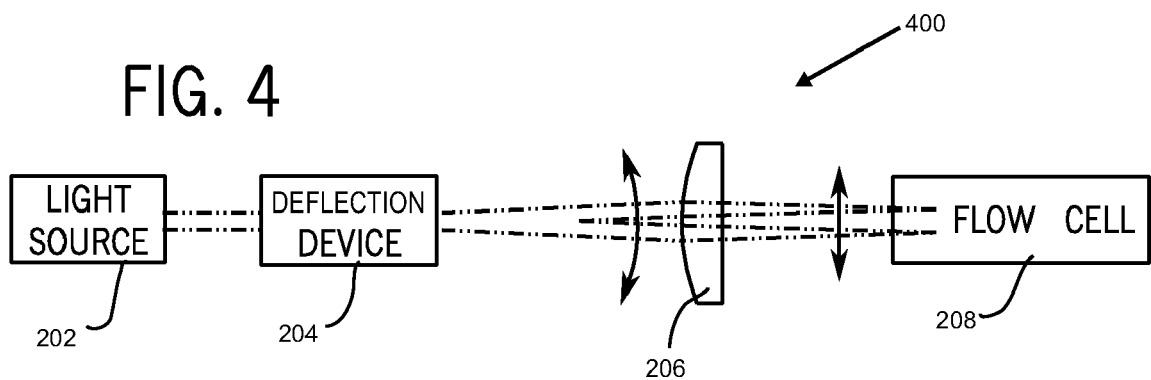

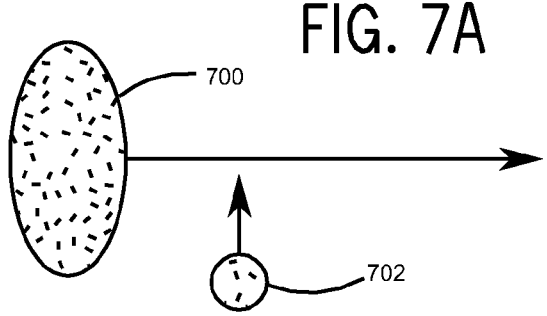
FIG. 7A
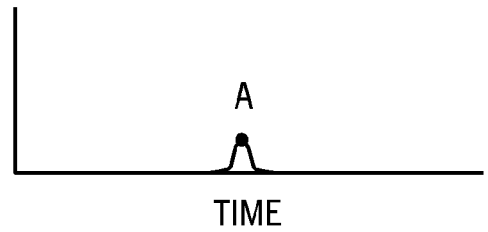
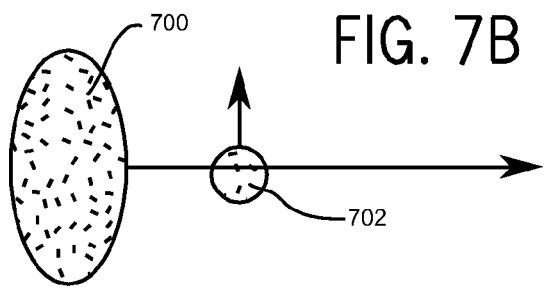
FIG. 7B
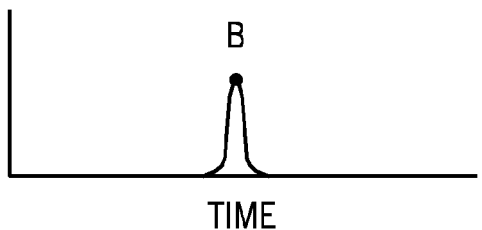
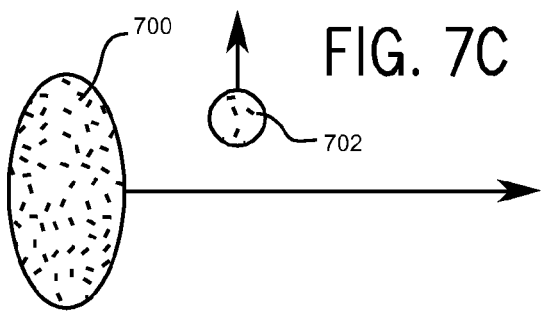
FIG. 7C
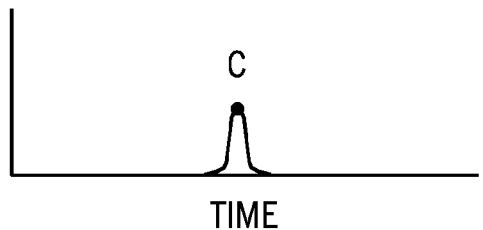
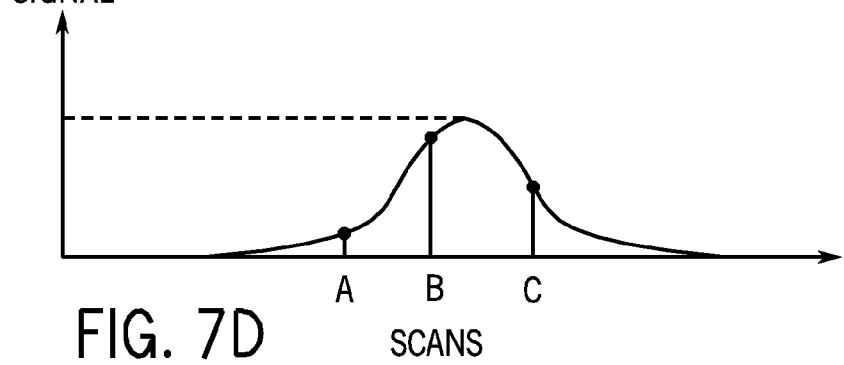
FIG. 7D

METHOD AND APPARATUS FOR RAPIDLY COUNTING AND IDENTIFYING BIOLOGICAL PARTICLES IN A FLOW STREAM

This application is a continuation application of U.S. application Ser. No. 12/880,523, filed Sep. 13, 2010, which is a divisional application of U.S. application Ser. No. 11/934,277, filed Nov. 2, 2007, now U.S. Pat. No. 7,804,594, which is a non-provisional application claiming priority from U.S. Provisional Application Ser. No. 60/877,874, filed Dec. 29, 2006.

BACKGROUND OF THE INVENTION

1. Field of the Invention

This invention relates to flow cytometers and hematology analyzers, and, more particularly, to hematology analyzers that count and identify biological cells using light scattering and fluorescence techniques in an optical flow cell.

2. Discussion of the Art

Flow cytometry is a technique for counting, examining, and sorting microscopic particles suspended in a stream of fluid. Flow cytometry allows simultaneous, multiparametric analysis of the physical and/or biochemical characteristics of single cells flowing through an optical/electronic detection apparatus. When used in hematology analyzers, flow cytometry enables the precise counting of cells in a measured volume of blood or other biological fluid sample and the identification of those cells based on the use of light scattering and/or fluorescence detection. As used herein, the phrase "flow cytometry" refers to the techniques and apparatus used in flow cytometers as well as in flow-cytometry-based hematology analyzers and other diagnostic instruments.

In flow cytometry, a beam of light, such as, for example, laser light of a single wavelength, light of a broader spectral nature from a light-emitting diode (LED), or some other source of light, is directed onto a hydrodynamically focused stream of fluid. A number of detectors are aimed at the region where the stream passes through the light beam, one or more detectors being in line with the light beam and typically several detectors positioned perpendicular to the light beam. The detector(s) in line with the light beam detect forward scatter, in one or more angular annuli or regions, or absorption or albedo, or both forward scatter and absorption or albedo. The detectors positioned perpendicular to the light beam detect side scatter, fluorescence, or both side scatter and fluorescence. Each suspended particle passing through the beam scatters the light in some way, and fluorescent chemicals in the particle may be sufficiently excited to emit light at a longer wavelength than that of the light source. The combination of scattered and fluorescent light is detected by the detectors, and by analyzing fluctuations in intensity at each detector (typically one detector for each desired fluorescent emission band and one detector for each annulus or region of scattering angles), it is possible to determine various facts about the physical and biochemical structure of each individual particle. Forward scatter correlates with the volume of the cell and side scatter depends on the complexity of the particle, such as, for example, the shape of the nucleus, the amount and type of cytoplasmic granules or the roughness of the cellular membrane. Fluorescent markers can be conjugated with monoclonal antibodies that selectively bind to certain types of cells or cells in a particular pathological state. Representative examples of instruments employing flow cytometers are described in U.S. Pat. Nos. 5,017,497; 5,138,181; 5,350,695; 5,812,419; 5,939,326; 6,579,685; 6,618,143; and U.S. Patent Publication 2003/0143117 A1. These patents describe a flowing stream of cells and a stationary beam.

A subfield of cytometry, laser scanning cytometry (LSC), involves scanning a laser beam across a field of interrogation. However, the field of interrogation is stationary, typically a section of a microscope slide to which cells have been adhered, and the measurement rate (i.e., the number of cells analyzed in a given unit of time) obtainable through such a scheme is far below what can be obtained by conventional flow cytometry. Furthermore, LSC is an imaging method suitable for detailed analysis of a relatively limited number of cells, whereas flow cytometry is a light-scattering and fluorescence-tagging method of analyzing large quantities of cells. (See, for example, U.S. Pat. Nos. 5,072,382, 5,523,207, and 6,002,788.) Two other techniques closely related to LSC are volumetric capillary cytometry (see, for example, U.S. Pat. No. 5,962,238) and microvolume LSC (see, for example, U.S. Pat. Nos. 6,603,537 and 6,687,395, and U.S. Patent Publication No. 2005/0280817). All of these techniques rely on a scanning laser beam impinging upon a specimen fixed to a controllable stage and on methods based on highly resolved imaging, confocal scanning, or spectroscopy techniques.

Several teachings in the prior art (see, for example, U.S. Pat. Nos. 5,083,014, 5,444,527, 5,521,699, 5,644,388, 5,824,269, 6,671,044, and 6,975,400, and U.S. Patent Publication Nos. 2002/0146734 and 2002/0057432) describe an imaging flow cytometer that combines the flow characteristics of a conventional analyzer with imaging capabilities. In the prior art, (a) the laser or other light source is stationary, necessitating the use of a charge-coupled detector (CCD) array in order to capture information from across the field of interrogation; and (b) the information obtained is of an imaging nature rather than of a scattering nature. This approach causes the process to run significantly more slowly than in flow cytometry; in other words, in order to obtain more detailed information for each cell by the use of the disclosed imaging strategy, the measurement rate is reduced, i.e., the overall number of cells actually analyzed in a given unit of time is reduced.

One of the key advantages of imaging methods is that such methods are capable of capturing fine details of individual cells, which enable a trained professional to make positive identifications in borderline cases. However, the greater detail obtainable by imaging methods are balanced by the reduction in the total number of cells that can be analyzed in this way in a given period of time. In methods based on scattering, identification is based on characteristics that are averaged over the cell (such as cell size, hemoglobin content, lobularity of the nucleus, etc.); however, the loss of fine detail in individual cells is compensated for by the ability to collect desired information for tens of thousands of cells in a matter of seconds. Such information can be used to plot the results in aggregate according to a few characteristics (such as, for example, size, lobularity, etc.).

The CELL-DYN® Sapphire® hematology analyzer (commercially available from Abbott Laboratories), an instrument based in part on flow cytometry, processes a minimum of 105 complete blood count (CBC) samples per hour under standard conditions (This aspect of performance is referred to as the throughput of the instrument.). Other commercially available hematology analyzers are capable of processing up to 150 standard CBC samples per hour, although they usually result in higher rates of reflex testing, slide review, or both reflex testing and slide review. It would be desirable to increase the effective throughput of hematology analyzers (i.e., accounting for both the mechanical throughput and the rate of first-pass reportability) so as to be able to process a higher volume of standard CBC samples per hour than currently possible, while at the same time maintaining a low rate of reflex testing and slide review. This improvement would enable use of such an analyzer in a high-volume laboratory (reference laboratory or hospital core laboratory), which requires the processing of large numbers of standard, mainly normal, CBC samples per day with as few slide reviews as possible. It would also enable higher throughput of samples in any of the other laboratory environments where an analyzer is used.

There are several obstacles to higher throughput, such as, for example, loading samples, aspirating samples, dispensing samples, diluting samples, mixing samples, incubating samples, staging samples, delivering samples to the flow cell, and the time required for a sequential measurement of a series of samples. These obstacles can be thought of as bottlenecks, where the narrowest bottleneck determines the overall throughput of the instrument. The current narrowest bottleneck in the CELL-DYN® Sapphire® instrument is the time involved in the sequential measurements through the optical flow cell. The performance currently achieved involves a compromise between acceptable levels of coincidences, acceptable precision of results (total number of cells counted), constraints from the present hardware/electronics architecture, i.e., arrangement of hardware and electronic components, and constraints from the assay strategy involving reagents and dilution. As used herein, a "coincidence" is interpreted to mean an event where two or more cells, either of a similar type or a dissimilar type, are sufficiently close that they cannot be resolved by the instrument, are counted as one, and are misidentified in one or more detection parameters.

Increasing the flow rate through the flow cell by widening the sample stream, by increasing the velocity of the sample stream, or both of the foregoing, have all been attempted. In a conventional flow cytometer, where the sample stream is intersected by a stationary beam, the measurement rate in the linear regime (defined as the number of cells being analyzed per second, n) is given by $$n = \rho x_{stream} z_{stream} v_{stream} \quad (\text{Eq. 1})$$

where $\rho$ represents the concentration of cells in the sample stream, $x_{stream}$ represents the transverse dimension of the illuminated portion of the sample stream, $z_{stream}$ represents the longitudinal dimension of the illuminated portion of the sample stream, and $v_{stream}$ represents the flow velocity. In order to increase the measurement rate, one can attempt to increase any one of those four quantities. However, under the circumstances encountered in the state of the art, increasing $\rho$ leads to greater coincidence events, as does increasing $x_{stream}$ and $z_{stream}$. Increasing $v_{stream}$ can lead to risks related to the onset of turbulence or other kind of hydrodynamic instability, which can severely reduce the precision of the measurements, because the resulting sample stream oscillates or fluctuates unpredictably across a stationary light beam.

Other options include simply doubling the entire measurement hardware, with two sets of measurements occurring in parallel on separate flow cells interrogated by separate sources of light. Two sources of light can be employed or a single source of light can be split into two. The shortcomings of this approach are increased complexity, a greatly increased cost, a greatly increased risk to reliability because of the large number of additional components, and increased service costs.

It would be desirable to improve throughput of a flow cytometer without incurring higher coincidences, without degrading precision of results, without significantly changing the hardware and/or electronics (and consequently having to meet most of the same constraints), without changing the chemistries and dilutions currently in use, and while maintaining the currently available desirable attributes associated with a high rate of first-pass reportability of results.

SUMMARY OF THE INVENTION

This invention provides a method for increasing the measurement rate of a flow cytometer, or of a hematology analyzer employing a flow cytometer, by utilizing the technique of laser rastering. Laser rastering involves sweeping a laser beam across a flowing sample stream in a hematology analyzer.

In a conventional flow cytometer, the stationary laser beam, generally significantly widened in the horizontal direction, intersects the comparatively narrow flowing sample stream, interacting with the cells or other particles therein and resulting in scattering or fluorescent signals that can be detected. According to the method described herein, the sample stream is given a width greater than that of a sample stream in a conventional hematology analyzer, thereby increasing the flow rate of cells through the flow cell. Referring to Eq. 1, this widening operation, in effect, increases the transverse dimension $x_{stream}$ of the sample stream, thereby increasing n by a proportional amount. However, this widening operation also increases the likelihood of potential coincidences.

In order to limit coincidences to acceptable levels, the spot of focused light from the light beam is reduced in the horizontal dimension so as to intercept only a portion of the resulting sample stream. Because the coincidences are governed by the magnitude of the volume of the sample stream illuminated at any one time by the laser beam, reducing the width of the laser beam to intersect only a portion of the transverse horizontal extent of the sample stream also reduces the magnitude of the illuminated volume. Such reduction is gauged to recover the size of the illuminated volume in the original, conventional design, where the coincidence rates are known and acceptable.

With a stationary laser beam, such a configuration would however "miss" a sizable portion of the sample stream, because the laser beam would now be narrower than the sample stream. In order to count all the cells (or particles) in the sample stream as they flow past the position of the focused laser beam, the laser is "rastered," or swept from side to side.

In conventional raster schemes, a spot is first moved across a given row in a given direction, then the spot is moved downwardly to the next row, the spot is then moved in a direction opposite to that traversed for the first row, the spot is again moved downwardly to the next row, and the procedure is repeated for the remaining rows in the area of interest. Alternatively, after moving across any given row, the spot is then moved downwardly by one row as well as back across so as to start the next row on the same side as the previous one. (An example of a conventional raster scheme is the formation of a television image on a standard CRT screen.) In this invention, rastering results from a combination of the transverse motion of the laser beam and the vertical translation of the flowing sample stream. In other words, the laser beam only needs to be swept in the horizontal direction, because the flowing sample stream provides the vertical translation of the interrogation volume necessary for rastering. The rastering is carried out at a sufficiently high speed to allow the laser beam to interact with all the cells or particles in the sample stream, with the result that the measurement rate is increased in direct ratio to the increase in the overall quantity $x_{stream} z_{stream} v_{stream}$ in Eq. 1 (assuming the cell concentration, or dilution level, $\rho$ is kept unchanged).

To account for the varying scattered intensities derived from the interaction of the cells with different portions of the profile of the laser beam, the raster speed and flow speed can be adjusted so as to interrogate every cell a plurality of times and obtain from this set of measurements a representative value of the peak scattered intensity.

In one embodiment, the apparatus and method of this invention employ: (a) a dynamic beam deflector (e.g., an acousto-optic modulator, hereinafter alternatively referred to as "AOM"; or an acousto-optic deflector, hereinafter alternatively referred to as "AOD") as the preferred type of component for effecting the sweeping of the light beam; (b) for each detector channel, one of each of the following components: a fast analog-to-digital converter (ADC) channel, a field-programmable gate array (FPGA) or portion thereof, and optionally a digital signal processing (DSP) chip or portion thereof; and (c) sufficient onboard memory registers to hold intermediate values for computation and storage. Additional electronic components, of both analog and digital nature, may be employed in order to provide the necessary signal conditioning steps in conjunction with the digitization and digital signal processing steps carried out by the elements in (b) and (c) above. These may include, but are not limited to, preamplifier circuitry with sufficient bandwidth, noise filtering circuitry, baseline restoration circuitry, and circuitry for compensation of light intensity variations; each of these may interact with the FPGA (and optionally with the DSP) and other circuitries in order to properly carry out its intended function. The other components of the analyzer are essentially similar to those conventionally used in current hematology analyzers and flow cytometers.

BRIEF DESCRIPTION OF THE DRAWINGS

FIG. 3 is a schematic diagram illustrating a sample stream that allows more cells to flow through the volume under analysis in a given unit of time. The relatively long major axis of the laser beam is greatly reduced in length in order to interrogate, typically, only one cell at a time. The laser beam sweeps across the significantly widened sample stream in order to intersect each cell as it flows within the sample stream.

FIG. 4 is a schematic diagram illustrating the essential components of a rastering flow cytometer according to the present invention.

FIG. 6A shows the laser beam initially contacting the cell. FIG. 6B shows the laser beam significantly overlapping the cell. FIG. 6C shows the laser beam centered on the cell, with the resulting interaction being at a maximum value. FIG. 6D shows the laser beam significantly, but not maximally, overlapping the cell. FIG. 6E shows the laser beam making its final contact with the cell.

FIGS. 7A, 7B, 7C, and 7D are schematic diagrams, along with graphs, illustrating multiple successive interactions of a laser beam with a cell as the cell advances within the sample stream, as the laser beam, which has a standard Gaussian profile, sweeps across the cell a plurality of times in consecutive raster scans. In each of FIGS. 7A through 7C, inclusive, the graph positioned on the right of each diagram illustrates the time-varying signals resulting from each interaction, along with the highest value of each signal. FIG. 7A shows the result of an interaction wherein the laser beam first contacts a cell. FIG. 7B shows the result of an interaction wherein the same call as in FIG. 7A has advanced further in the sample stream and interacts relatively close to the central portion of the laser beam. FIG. 7C shows the result of a third interaction wherein the same cell as in FIGS. 7A and 7B has advanced further in the sample stream and interacts with the edge of the laser beam. FIG. 7D indicates the highest values arranged by scan number (or time) on the graph, a curve (e.g., a Gaussian curve) that is mathematically fitted to these values, and the peak value of that curve.

FIG. 10 shows the dimensional parameters utilized to explain the condition of coincidences.

FIG. 11 illustrates how the overall volume of illumination (and therefore the coincidence rates) can be maintained substantially constant, while one or more of the dimensional parameters are varied with respect to the prior art.

FIGS. 12, 12B, and 12C show the dimensional parameters utilized to explain the requirement that each interaction provide a plurality of digitized measurements.

FIG. 13 shows the dimensional parameters utilized to explain the requirement that the laser beam sweep across the cell a plurality of times as the cell advances in the sample stream.

FIG. 14 shows the dimensional parameters utilized to calculate the overall measurement rate of the system (i.e., the number of cells measured in a given unit of time).

FIG. 15 illustrates how the number of cells measured in a given unit of time can be increased while one or more of the dimensional parameters are varied with respect to the prior art.

DETAILED DESCRIPTION

As used herein, the expression "laser rastering" refers to the novel method and apparatus described herein. However, it should be noted that the term "laser" is intended to include any source of light suitable for use in this invention. Such sources of light include, but are not limited to, lasers, light-emitting diodes (LEDs), arc lamps, plasmas, and any other source of light that is capable of providing sufficient brightness, stability or reproducibility or both stability and reproducibility of intensity and wavelength, and spectral purity. Likewise, in the description that follows, a laser will be referred to as an example of a suitable source of light, without implying that other sources of light are not included in the description of this invention. As used herein, the term "deflect" means to move a beam of light across a sample stream in a flow cell. Alternate expressions used herein which are intended to have substantially the same meaning as "deflect" include "scan" and "sweep." The expression "imaging method" refers to a method that is different from a scattering method. The expression "sample stream" means a body of running fluid, in a flow cell, in which particles from a biological sample are carried. The sample stream (e.g., a body fluid such as, for example, blood, optionally mixed with a saline solution or with a reagent solution) is typically surrounded by a sheath of fluid (e.g., phosphate buffered saline) that flows alongside of it within the flowcell, and which both provides isolation from the flowcell walls and confines the sample stream to a smaller portion of the flow cell. The term "rastering" means repeatedly sweeping a beam from a source of light from side to side. As used herein, the term "particle" is intended to include a biological cell and any other biological or non-biological substance having a size ranging from about 0.5 µm to about 50 µm in major dimension, e.g., diameter. In the description that follows, a cell will be referred as just one example of a suitable item presented to the apparatus for analysis; other items, such as, for example, cell fragments, nuclei, other biological particles (e.g., bacteria), or non-biological particles (e.g., beads of silica, latex, or other material, either pure or augmented, by coating, inclusion, mixing, or other method, with fluorescent substances; and either untreated or treated with conjugated monoclonal antibodies or other biological markers for use in rapid screening and other similar assays), are also included in the scope of the term "particle". As used herein, the expression "source of light" and the expression "light source" are interchangeable.

Figure 9:
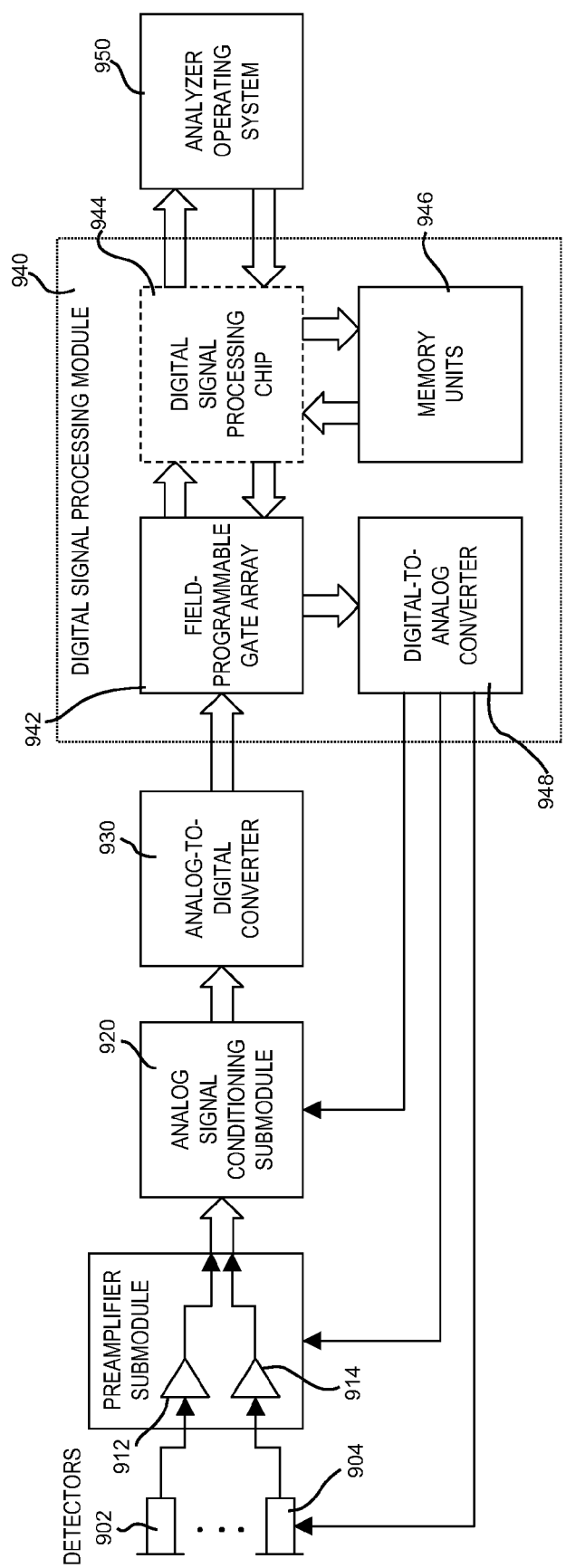
FIG. 9 is a schematic block diagram of the essential elements of the electronic module used for signal processing in the present invention.

The system comprises two key modules: (1) an optical module to effect the angular sweep across the sample stream, and (2) an electronic module to process the signals derived from the optical module. The optical module described herein, with the exception of detectors, filters, and other peripheral optical components, is shown in FIG. 4. The configuration of the present invention (in a schematic view) is contrasted with the configuration of the prior art. The optical module of the present invention includes a deflection device, e.g., an acousto-optic modulator (AOM) or acousto-optic deflector (AOD), inserted into the optical path. The electronic module described herein is shown in FIG. 9, and it includes fast analog-to-digital converter(s) (ADC), field-programmable gate array(s) (FPGA), and optionally digital signal processing (DSP) chip(s).

The AOM is an addition to commercially available hematology analyzers currently in use. The components in the electronic module are in part substitutions for electronic components currently in use and in part additions to electronic components currently in use.

Figure 1:
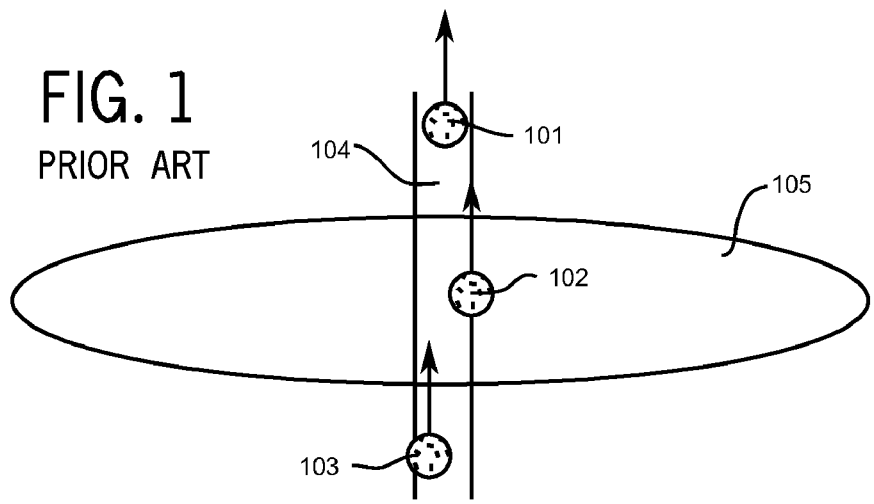
FIG. 1 is a schematic diagram illustrating the prior art from the point of view of the laser beam. The focused beam spot is elliptical with a relatively short minor axis (shown here as the vertical axis) and a relatively long major axis (shown here as the horizontal axis). The laser beam intersects the narrow sample stream so as to interrogate substantially only one cell at a time.

Referring now to FIG. 1, the method of obtaining data from flow cytometry equipment typically used in the prior art involves illuminating cells 101, 102, 103 moving with the sample stream 104 by means of a stationary source of light 105, e.g., a laser beam. In FIG. 1, it can be seen that the spot (focus) of the source of light 105, e.g., a laser beam, is elliptical in shape, with a relatively short minor axis (y) and a relatively long major axis (x); additionally, such a spot typically has an intensity profile (along either the short or the long axis) approximately described by a Gaussian curve.

Figure 2:
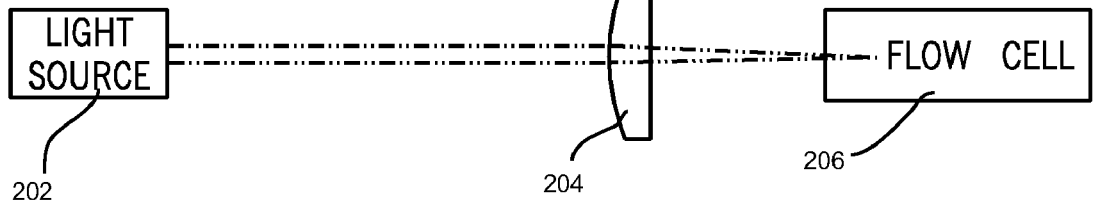
FIG. 2 is a schematic diagram illustrating the essential components of a conventional flow cytometer of the prior art.

The method shown diagrammatically in FIG. 1 can be carried out by the optical module depicted in FIG. 2. The optical module 200 shown in FIG. 2 comprises a source of light 202, a lens or system of lenses 204, a flow cell 206, and detectors (not shown). For the sake of simplification, detectors, which are required, are not shown, but are well-known to those of ordinary skill in the art. Other peripheral or optional components, such as mirrors, slits, prisms, and filters, are also not shown. The electronic module is also not shown.

In the prior art, as depicted in FIG. 1, each cell 101, 102, 103 is presented a varying light beam profile in the direction of flow (vertical dimension) and a substantially uniform light beam profile over the width (horizontal dimension) of the sample stream 104 (because the beam of light 105 in the horizontal direction is made very much wider than the sample stream 104); in the prior art, the peak is found in the vertical dimension, i.e., the direction of flow.

Referring now to FIG. 3, the method of this invention involves illuminating cells 301, 302, 303, 304, 305, 306, 307, 308, 309 moving with the sample stream 310 by means of a source of light 311, e.g., a laser beam, which is caused to raster by means of a deflection device. It can be seen that the spot (focus) of the source of light, e.g., the laser beam, is elliptical in shape, with the major axis (y") being substantially equal in length to the minor axis (y) of the beam of the prior art and the minor axis (x") being substantially shorter than the major axis (x) of the beam of the prior art. In FIG. 3, the spot (focus) of the laser beam is caused to sweep across the flow stream in a direction parallel to the minor axis (x").

The method shown diagrammatically in FIG. 3 can be carried out by the optical module shown schematically in FIG. 4. In FIG. 4, the essential components of the optical module 400 are a source of light 402, a deflection device 404, at least one optical element such as, for example, a lens or system of lenses 406 for focusing light from the source of light 402, a flow cell 408, and at least one detector (not shown). For the sake of simplification, detectors, at least one of which is required, are not shown, but are well-known to those of ordinary skill in the art. Other peripheral or optional components, such as mirrors, slits, prisms, and filters, are also not shown. The electronic module is also not shown.

In the scheme of the invention described herein and depicted in FIG. 3, each cell 301, 302, 303, 304, 305, 306, 307, 308, 309 is presented a varying profile in both the horizontal direction and in the vertical direction of the sample stream 310, because the beam of light 311 is made smaller than the width of the sample stream 310. The determination of peak intensity is then achieved in two steps. In the first step, peak intensity is determined "horizontally" (across) the sample stream 310, with rapid digitization and isolation of peaks from individual raster scans in the horizontal direction. In the second step, peak intensity is determined "vertically" in the sample stream 310 by analyzing multiple raster scans and fitting the sequence of peak values to a curve that represents the profile of the beam of light 311 in the vertical direction; alternatively, such a curve can be obtained by applying appropriate digital filtering to the sequence of peak values.

The deflection device 404 can be an AOM or an AOD. The essential components of systems of the prior art include a source of light, a lens or system of lenses, a flow cell, and appropriate detectors. No scanning or deflection device such as, for example, an AOD, is employed in the prior art of flow cytometry. In both the prior art and in the present invention, the sources of light, the lens and the systems of lenses, the flow cells, and the detectors, and the functions thereof in a flow cytometry system, are well-known to those of ordinary skill in the art. See, for example, U.S. Pat. Nos. 5,017,497; 5,138,181; 5,350,695; 5,812,419; 5,939,326; 6,579,685; 6,618,143; and U.S. Patent Publication 2003/0143117 A1, where sources of light, lenses, flow cells, and detectors are described in greater detail. All of these references are incorporated herein by reference. See also http://biology.berkeley.edu/crl/flow_cytometry_basic.html, Mar. 30, 2006, pages 1-7, incorporated herein by reference. Lasers, lenses, flow cells, and detectors suitable for use in this invention are used in commercially available instruments from Abbott Laboratories, Abbott Park, Ill., under the trademark CELL-DYN®.

AOMs, and their subset known as AODs, are well-known in the art of laser physics and optical technology. An AOM, also sometimes known as a Bragg cell, uses the acousto-optic effect to dynamically diffract, and thereby to deflect, a beam of light using sound waves (usually at radio frequency). An AOM can also be used to shift the frequency of the light beam. AOMs are used in lasers for Q-switching, in telecommunications for signal modulation, and in spectroscopy. A piezoelectric transducer is attached to a material such as glass or quartz. An oscillating electrical signal drives the transducer to vibrate, which creates sound waves in the glass or quartz. These can be thought of as moving periodic planes of expansion and compression that change the index of refraction of the optical medium. Incoming light interacts with the resulting periodic index modulation in a process called Bragg diffraction, and is deflected at an angle with respect to the incoming beam direction. The properties of the light exiting the AOM can be controlled in five ways: (a) deflection, (b) intensity, (c) frequency, (d) phase, and (e) polarization. AOMs are much faster than typical mechanical devices, such as tiltable mirrors. The time it takes an acousto-optic modulator to alter the exiting beam is roughly limited to the transit time of the sound wave across the beam (typically 5 to 100 microseconds): this is sufficiently fast to create active modelocking in an ultrafast laser. Through careful design, transit times as low as a few hundred nanoseconds can be achieved. (It is noted that this represents the maximum time required to move the beam across the entire angular deflection range, and not the time necessary to deflect the beam from one angular position to one immediately adjacent to it. In other words, for specific applications, such as in the present invention, where the required sweeping is smooth across the scan range, considerably faster performance can be obtained than is the case for truly random-access deflection at an arbitrary angle. The only requirement is that there must be compensation for the amount of optical distortion potentially introduced into the light beam by the fast sweeping action by using a weak external optical element, such as a cylindrical lens.) AOMs offer fast response, good deflection range, simple solid-state design with no moving parts, and relatively low power consumption. Through the use of an AOM, a light beam is diffracted into several orders. By vibrating the material with a high-quality sinusoid and orienting the AOM to optimize deflection into the first diffraction order, up to 90% deflection efficiency can be achieved.

In one embodiment of this invention, flow cytometry systems currently available can be employed, whereby hardware and firmware changes are relatively minor. However, use of the laser rastering technique described herein will result in significant improvements in measurement rates. In the system of the present invention, a suitable deflection device is an acousto-optic modulator.

In the discussion that follows, the source of light is a laser beam. However, as stated previously, other sources of light can be used, such as, for example, lamps (e.g., mercury, xenon). Lasers include, but are not limited to, high-power water-cooled lasers (e.g., argon, krypton, dye lasers), low power air-cooled lasers (e.g., HeCd (UV), argon (488 nm), red HeNe (633 nm)); and diode lasers (violet, blue, green, red). The laser beam is assumed to have a varying intensity profile, such as, for example, a Gaussian profile, in two directions.

Figure 5:
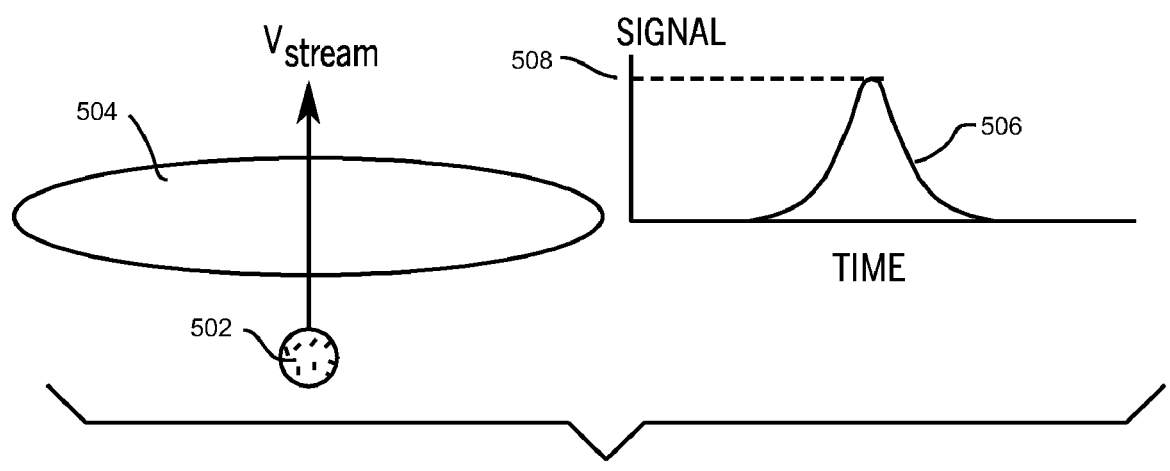
FIG. 5 is a schematic diagram illustrating the interaction of a cell with the laser beam in a conventional flow cytometer of the prior art, along with a graph indicating the conventional method of normalizing such an interaction by establishing and holding the peak value of the resulting signal.

Referring now to FIG. 5, in the prior art the cell 502 traverses the stationary light beam spot 504 as the cell 502 is carried along within the sample stream. As the cell 502 is exposed to portions of the beam spot 504 with varying intensity, the resulting amount of signal intensity 506 (initially in the form of scattered, or absorbed light, or emitted fluorescent light; and, after detection, in the converted form of electronic current or voltage) varies in accordance with the profile of the beam 504 in the direction (vertical in this depiction) traversed by the cell 502. In the prior art, this signal 506 is typically further detected by electronic circuitry that identifies the peak value 508 of the varying interaction between the light beam spot 504 and the cell 502 and stores it, typically in analog form, for subsequent digitization. This method of obtaining the value of interaction between a cell and a light beam is referred to in the prior art as "peak-and-hold."

Figure 6A:
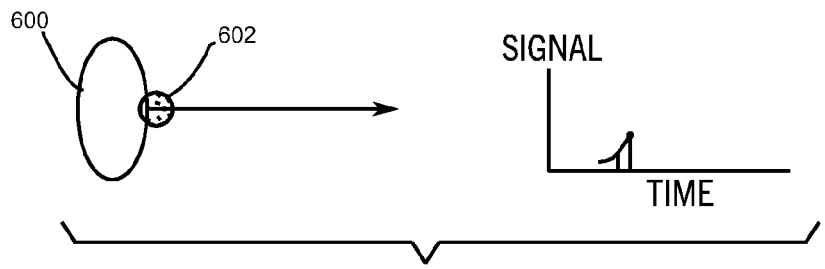
FIGS. 6A, 6B, 6C, 6D, and 6E are schematic diagrams, along with graphs, illustrating the interaction of a laser beam with a cell as the laser beam, which has a standard Gaussian profile, sweeps across the cell in the sample stream. In each of FIGS. 6A through 6E, inclusive, the graph positioned on the right of each diagram illustrates the value of the signal resulting from each interaction depicted, along with the values of the previous interactions.
Figure 6B:
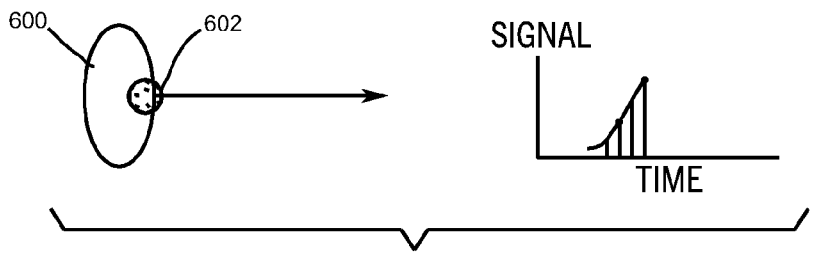
Figure 6C:
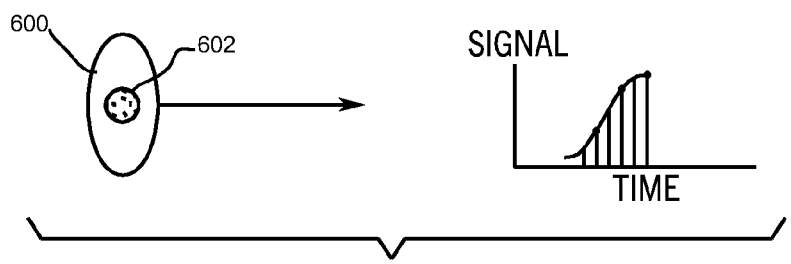
Figure 6D:
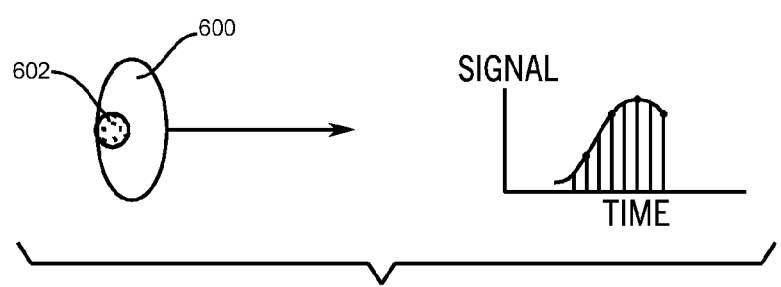
Figure 6E:
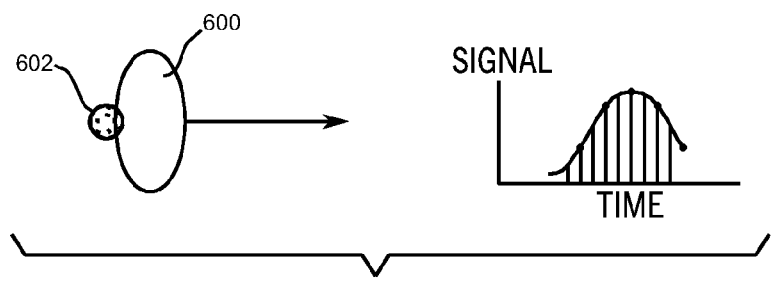
Figure 6F:
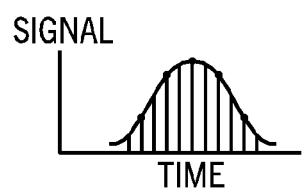
FIG. 6F indicates the intensity of the signal as a function of time, with representative values shown from the interactions illustrated in FIGS. 6A through 6E, inclusive.

Referring now to FIG. 2 for the present invention, the beam is swept across the sample stream. As the beam is swept across the sample stream, each of the signals from the detectors (after suitable conditioning by circuitry described below) is sampled at a high frequency by an analog-to-digital converter (ADC). FIGS. 6A, 6B, 6C, 6D, and 6E show this process for the signal from one representative detector channel. These signals are generated by scattered or absorbed light or emitted fluorescent light. The peak value of the series derived from the full interaction with a cell is stored for later use. FIGS. 6A, 6B, 6C, 6D, and 6E are schematic diagrams, along with graphs, illustrating the interaction of a laser beam with a cell as the laser beam, which has a standard Gaussian profile, sweeps across the cell in the sample stream. In these figures, the beam traverses the cell, while the position of the cell is essentially fixed. In each of FIGS. 6A through 6E, inclusive, the graph positioned on the right of each diagram illustrates the value of the signal resulting from each interaction depicted, along with the values of the previous interactions. FIG. 6A shows the laser beam 600 initially contacting the cell 602. FIG. 6B shows the laser beam 600 significantly overlapping the cell 602. FIG. 6C shows the laser beam 600 centered on the cell 602, with the resulting interaction being at a maximum value. FIG. 6D shows the laser beam 600 significantly, but not maximally, overlapping the cell 602. FIG. 6E shows the laser beam 600 making its final contact with the cell 602. FIG. 6F indicates the intensity of the signal as a function of time, with representative values shown from the interactions illustrated in FIGS. 6A through 6E, inclusive.

Next, as the laser beam scans the sample stream in successive sweeps, the light from the laser beam interacts with each individual cell a plurality of times, as shown in FIGS. 7A, 7B, and 7C. Each of these interactions results in a peak value (for each detection channel), which is determined and stored. Because the interactions occur at different points on the beam profile, the interactions, in effect, sample the beam profile at discrete intervals—separated by the time it takes to complete a single raster cycle. The DSP unit collects the sequence of peak values attributed to a single cell and correlates them algorithmically to the profile of the laser beam. The peak of the thus fitted curve is then further processed by downstream algorithms, as in a conventional instrument, for cell identification and counting. For example, FIG. 7A shows the result of an interaction wherein the laser beam 700 first contacts a cell 702. FIG. 7B shows the result of an interaction wherein the same cell 702 as in FIG. 7A has advanced further in the sample stream and interacts relatively close to the central portion of the laser beam 700. FIG. 7C shows the result of a third interaction wherein the same cell 702 as in FIGS. 7A and 7B has advanced further in the sample stream and interacts with the shoulder of the laser beam 700. The rastering speed and the velocity of the sample stream must be set so that each cell is intercepted a plurality of times as it flows past the beam of light.

Figure 8A:
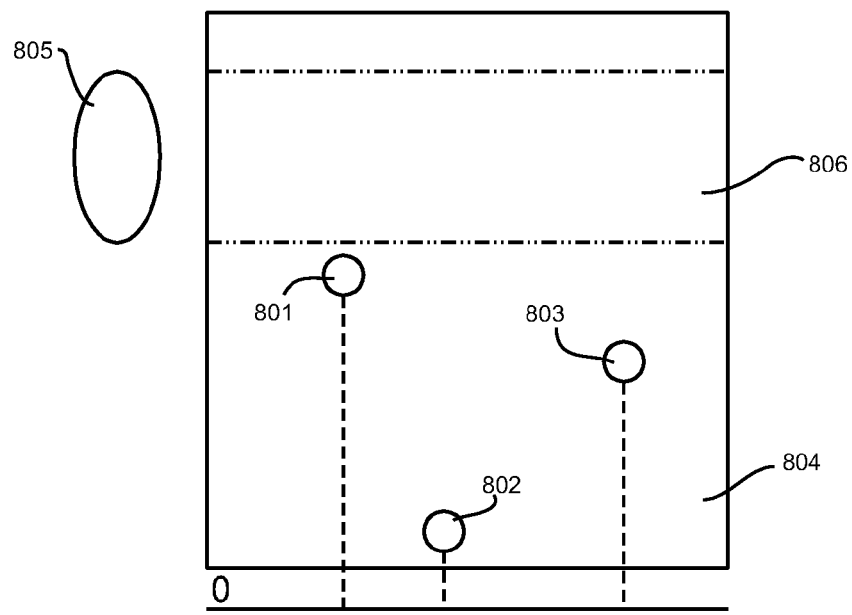
FIGS. 8A, 8B, 8C, 8D, 8E, 8F, 8G, 8H, 8I, 8J, 8K, 8L, and 8M comprise a series of schematic diagrams illustrating the spot of a laser beam interacting with several cells moving in a sample stream.
Figure 8B:
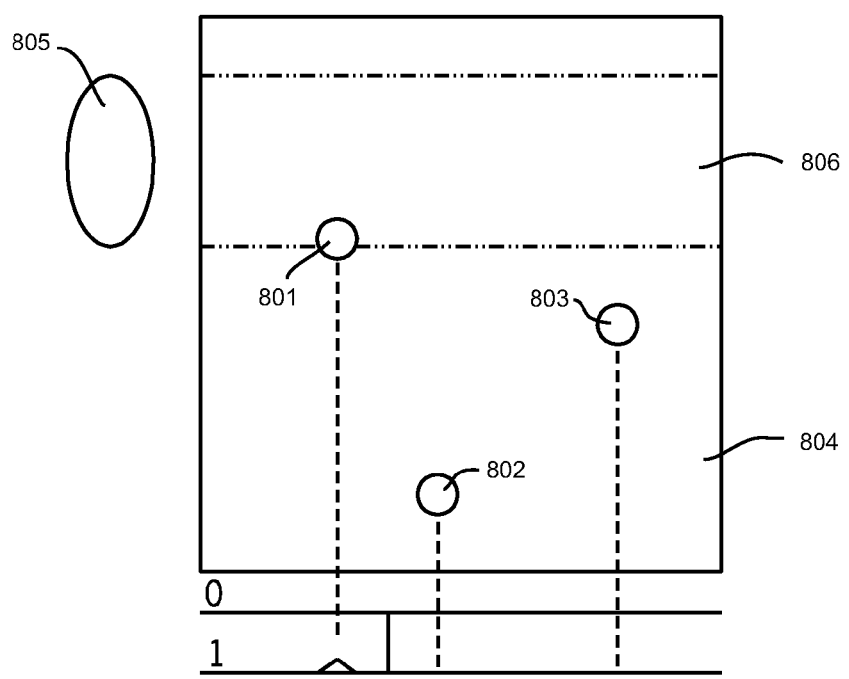
Figure 8C:
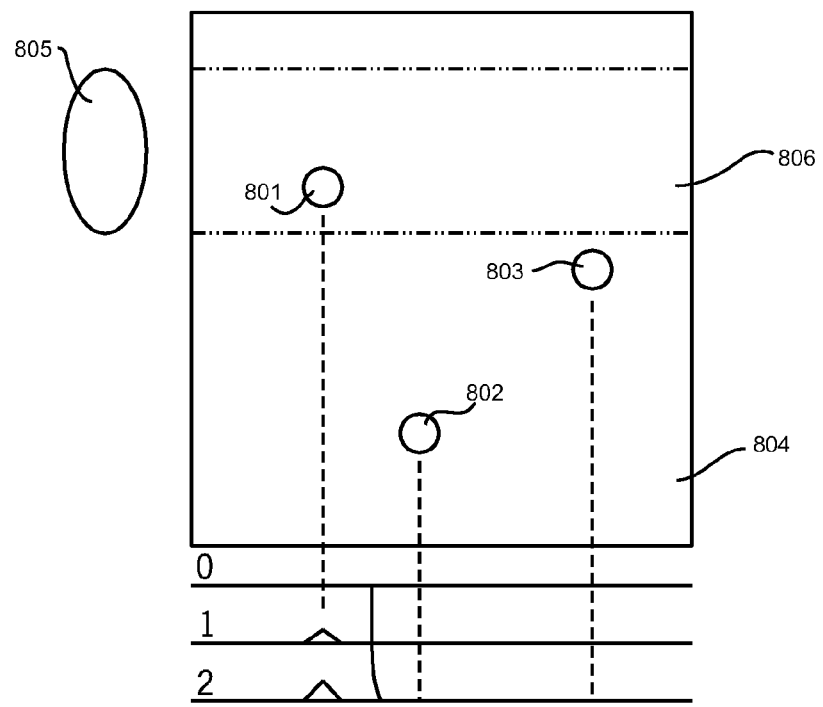
Figure 8D:
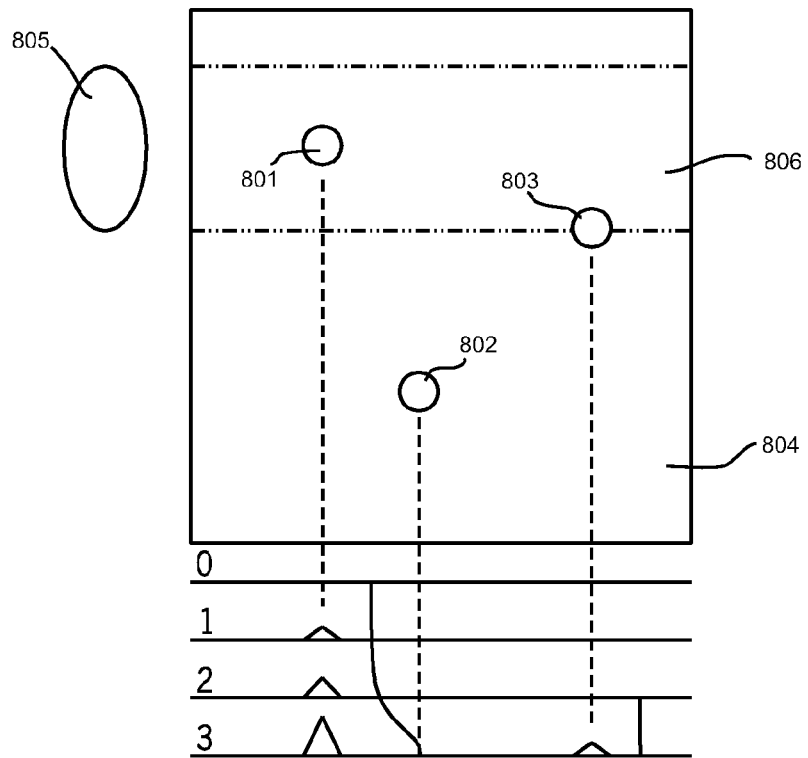
Figure 8E:
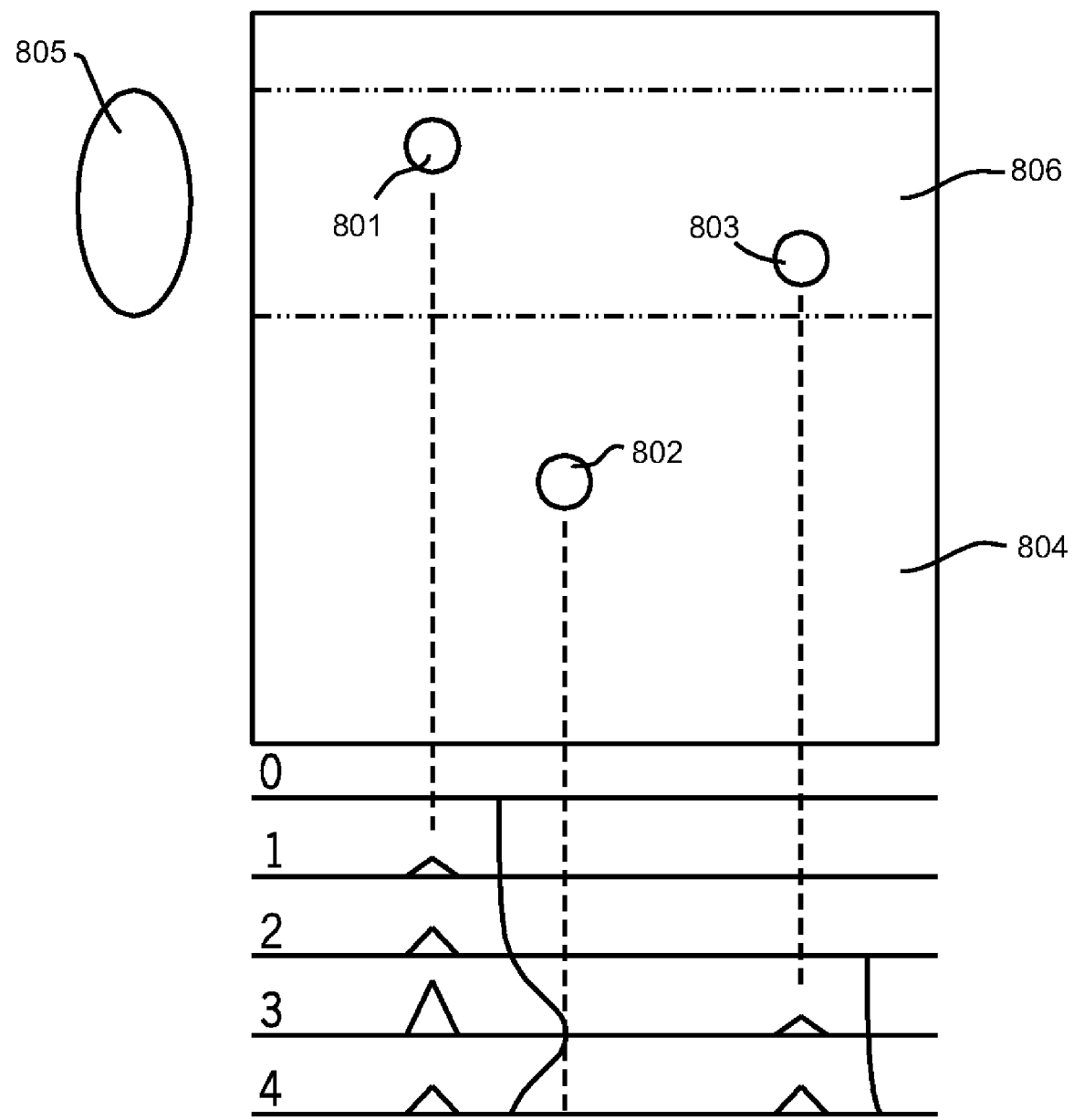
Figure 8F:
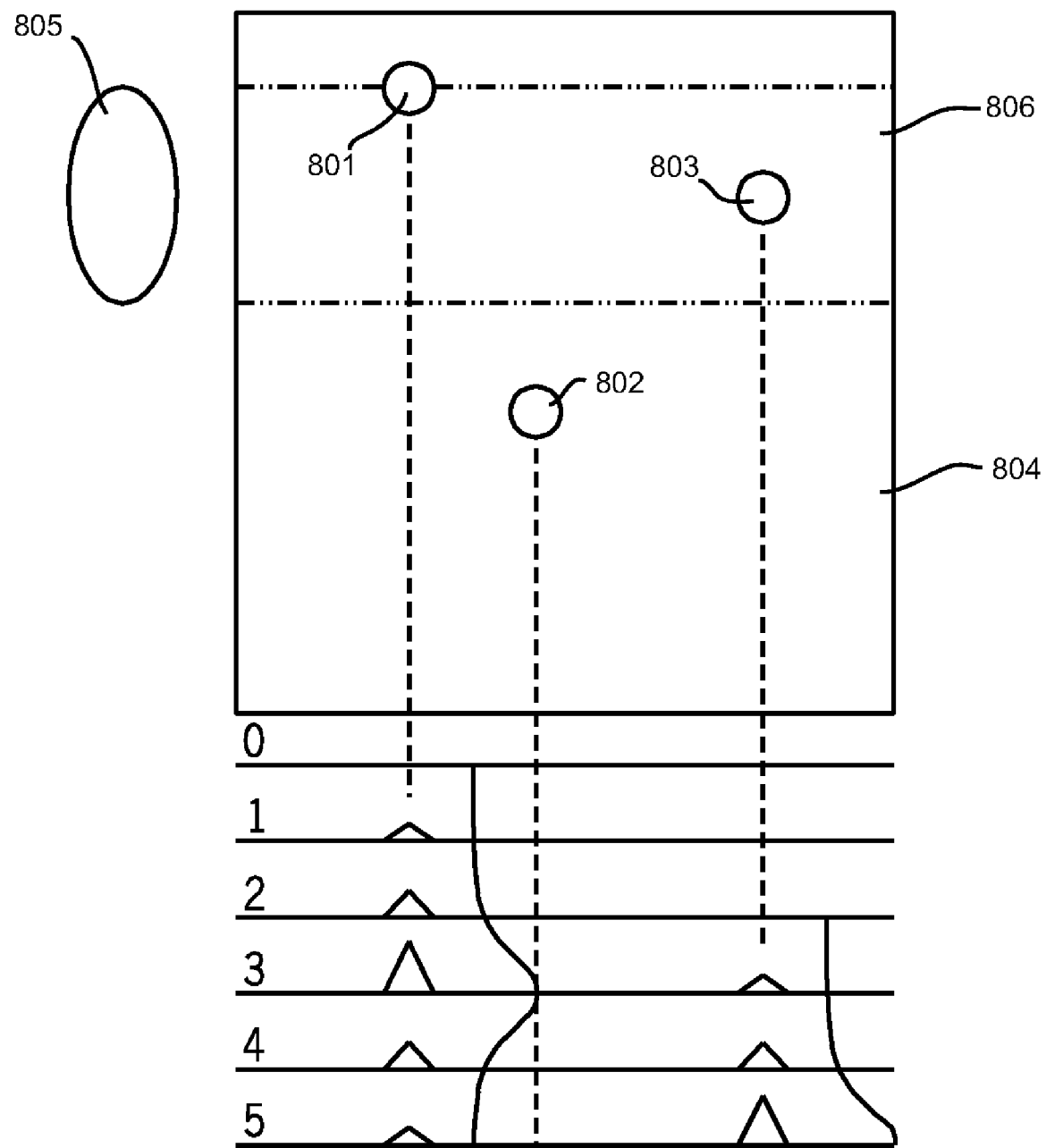
Figure 8G:
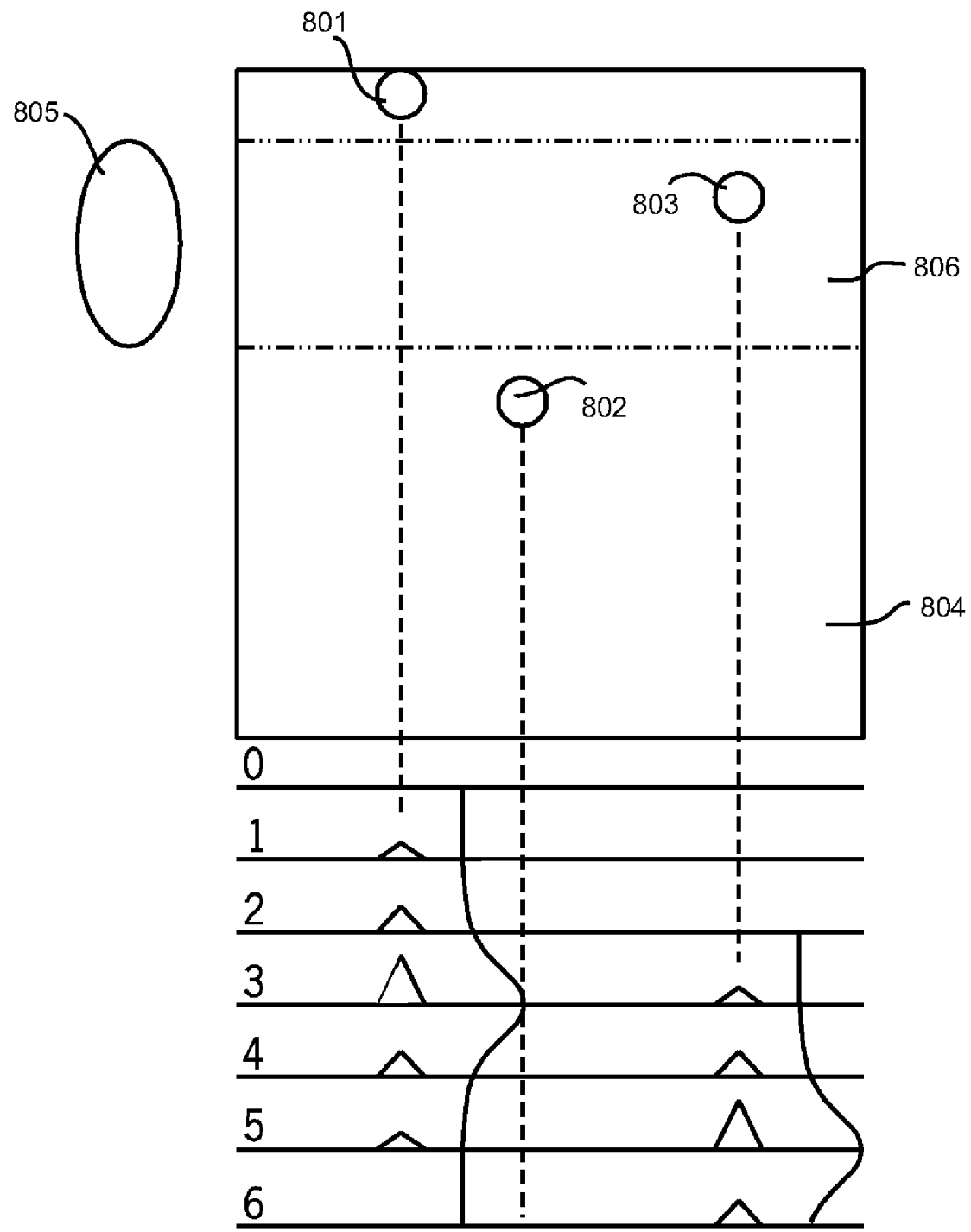
Figure 8H:
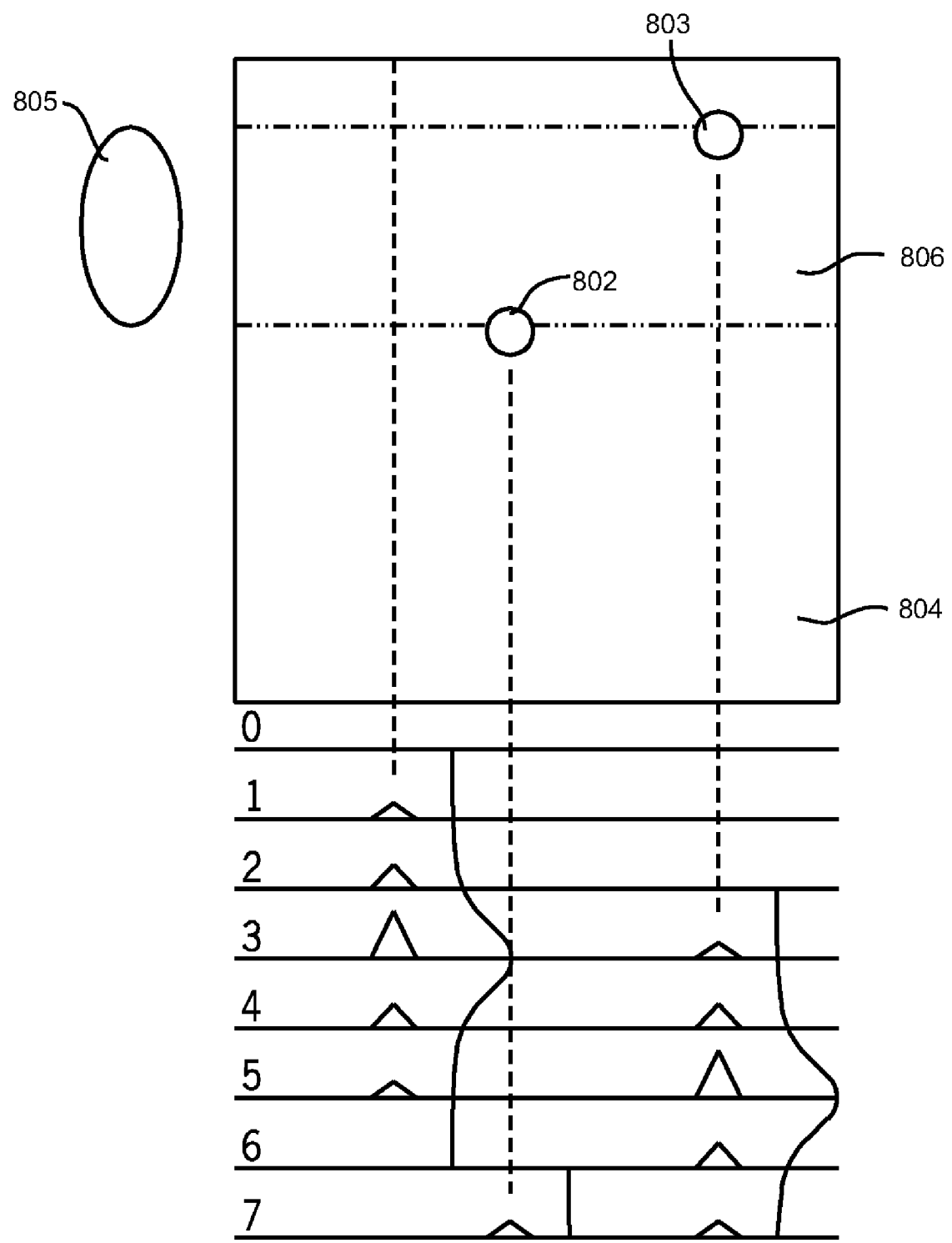
Figure 8I:
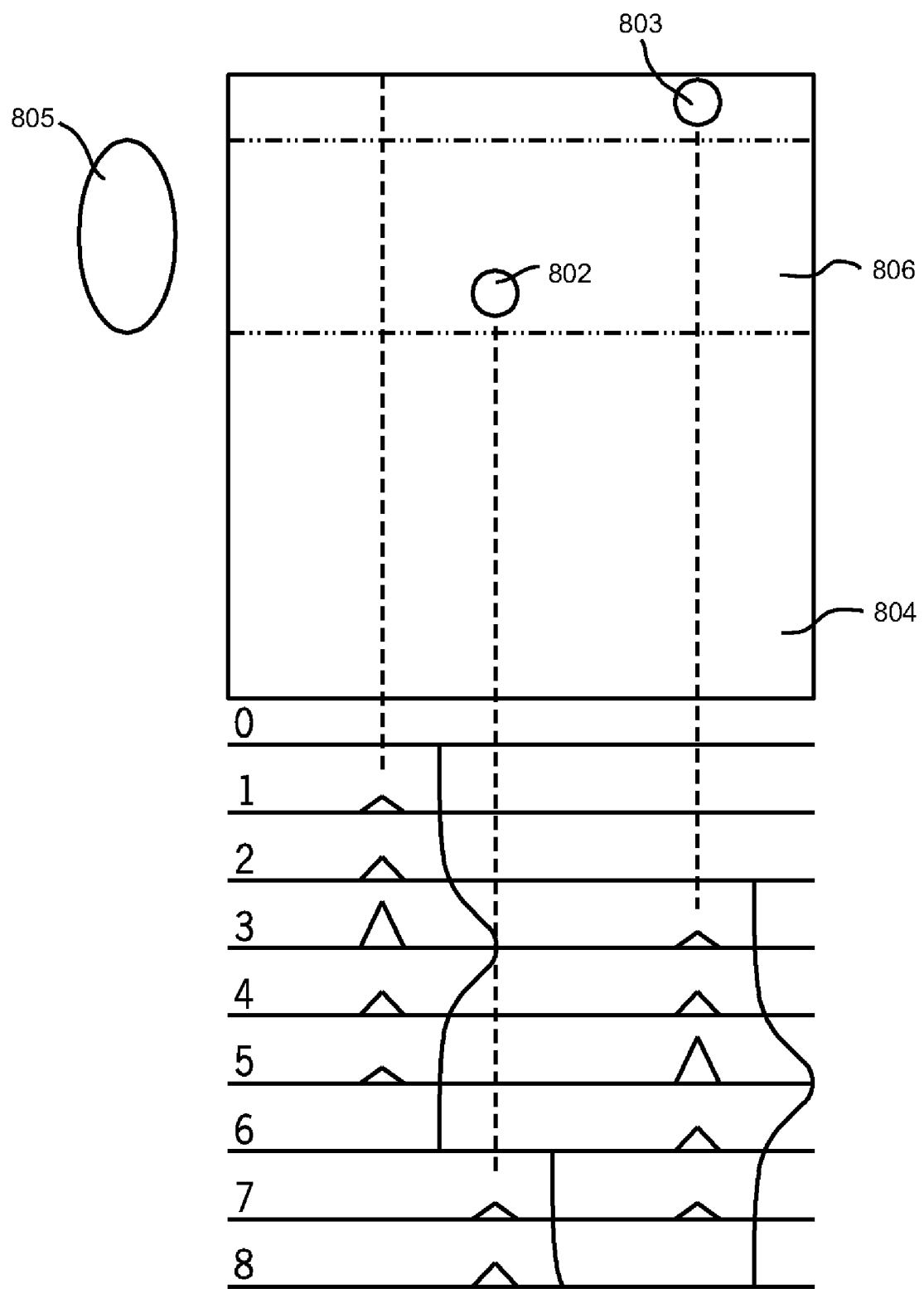
Figure 8J:
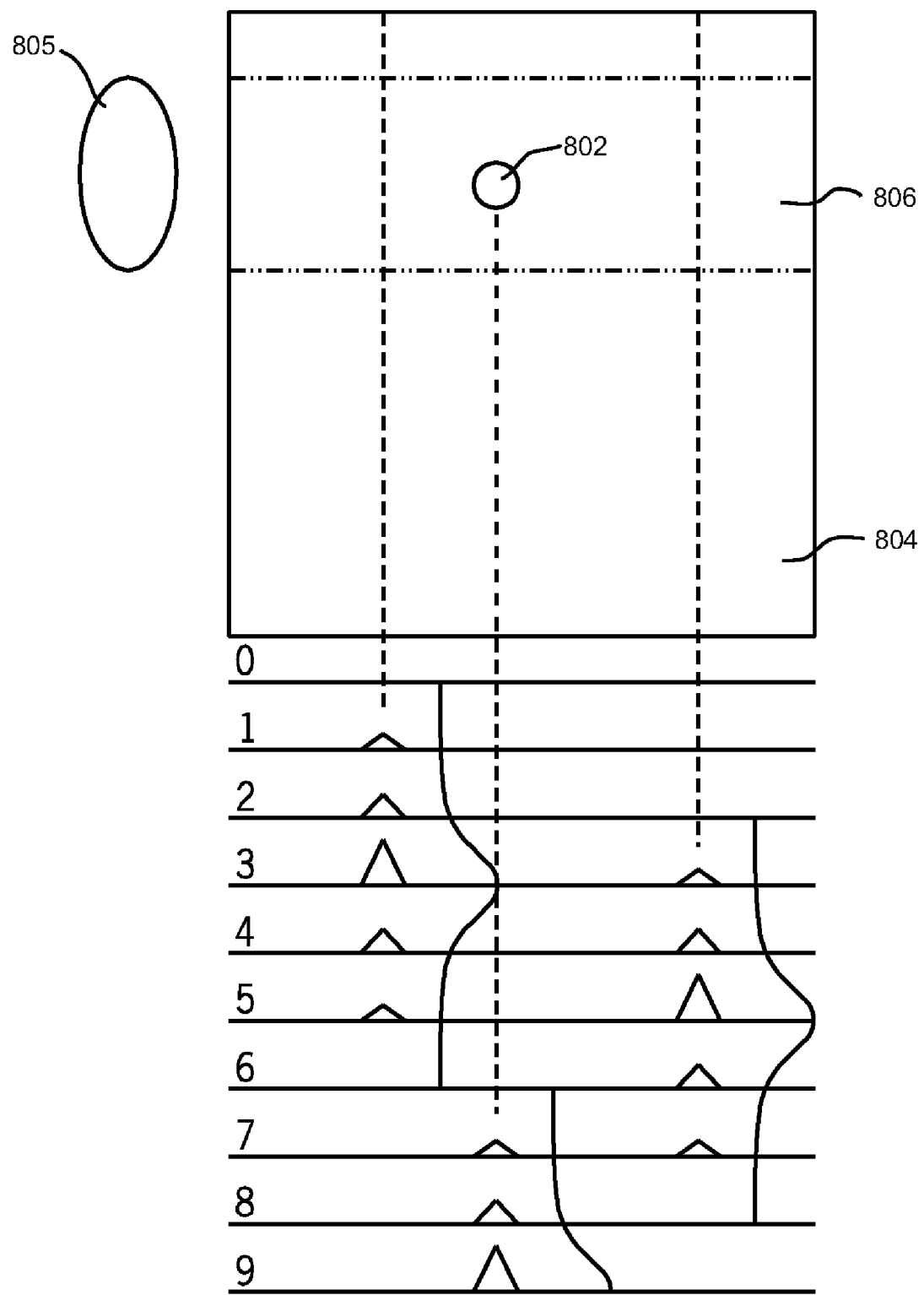
Figure 8K:
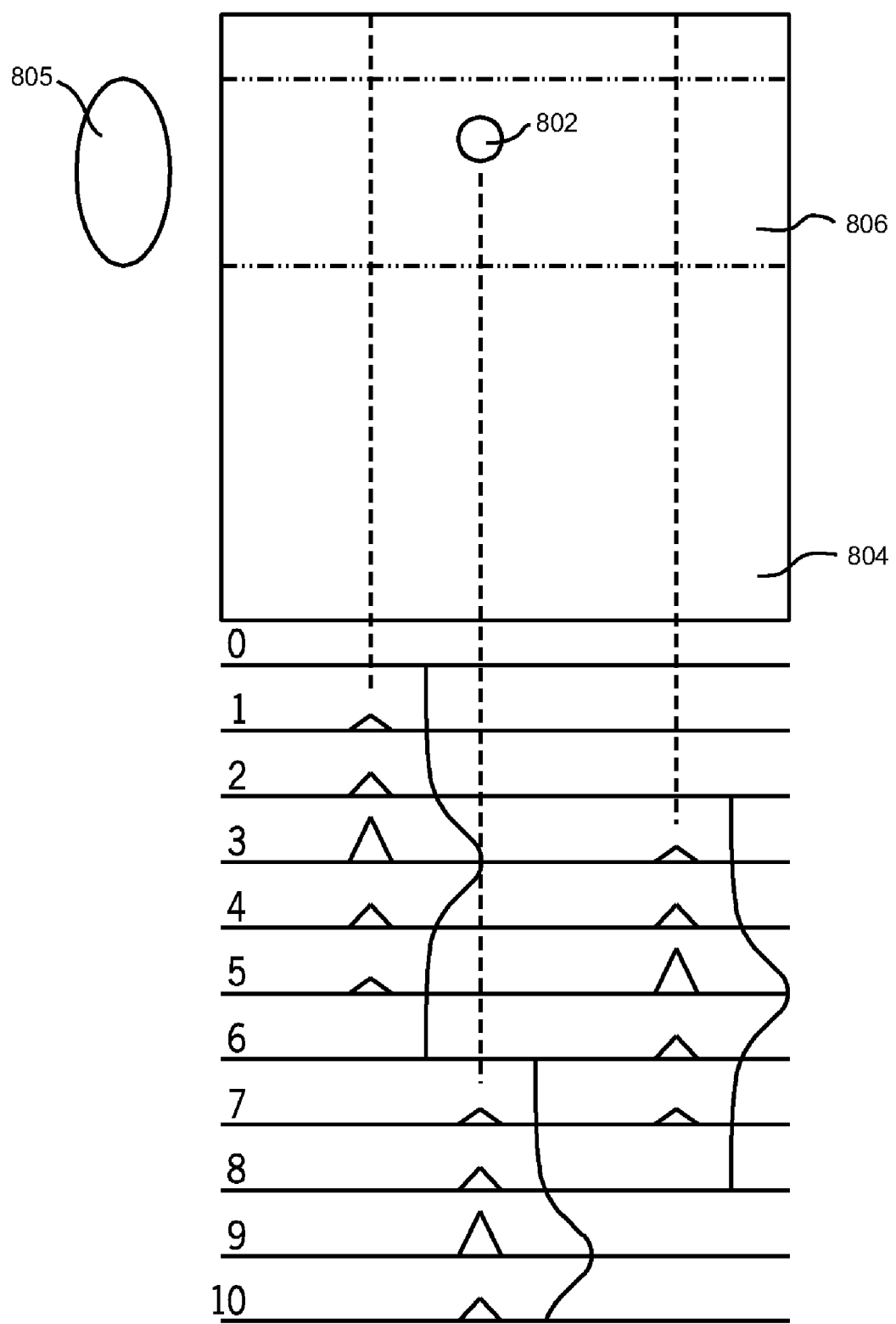
Figure 8L:
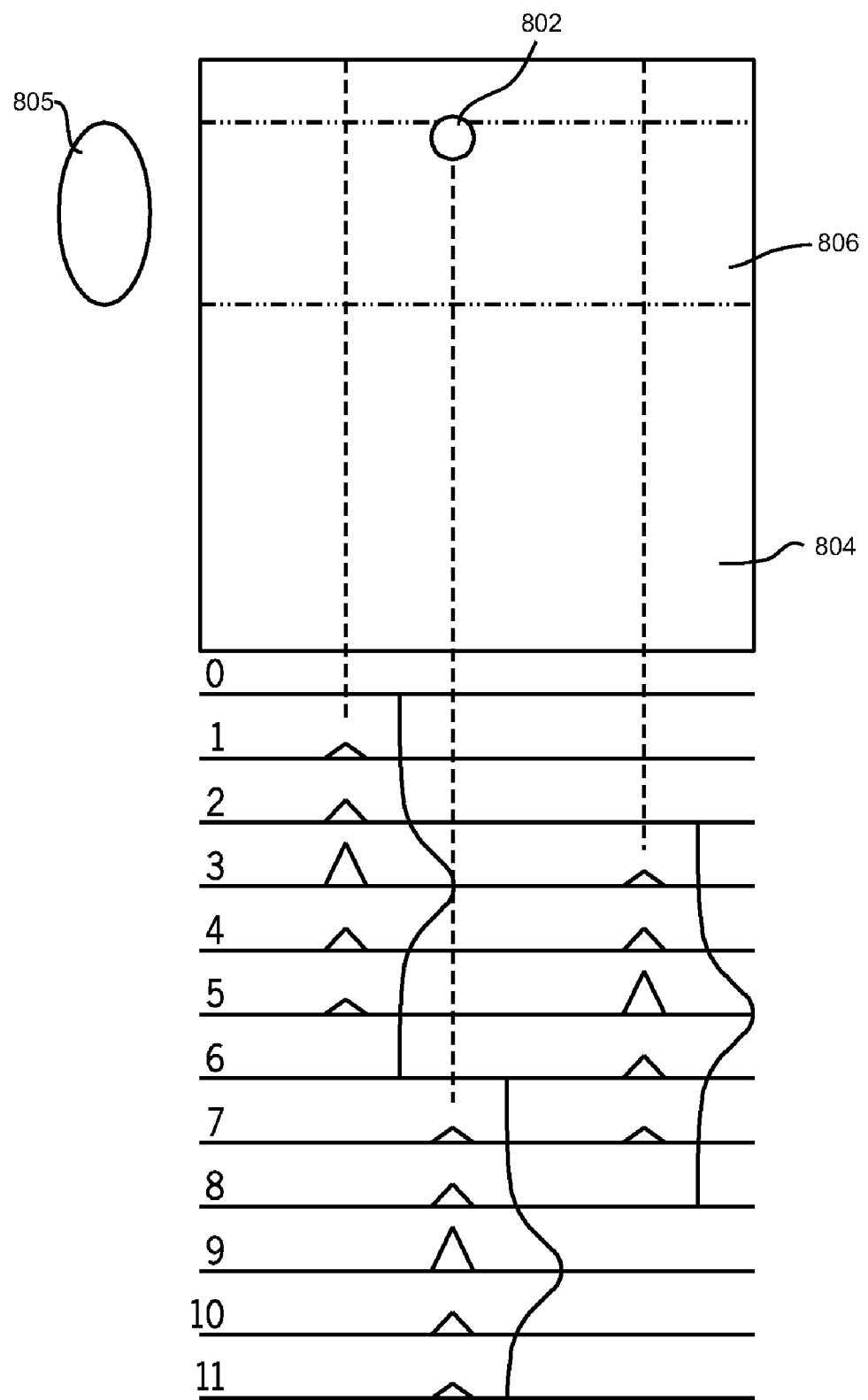
Figure 8M:
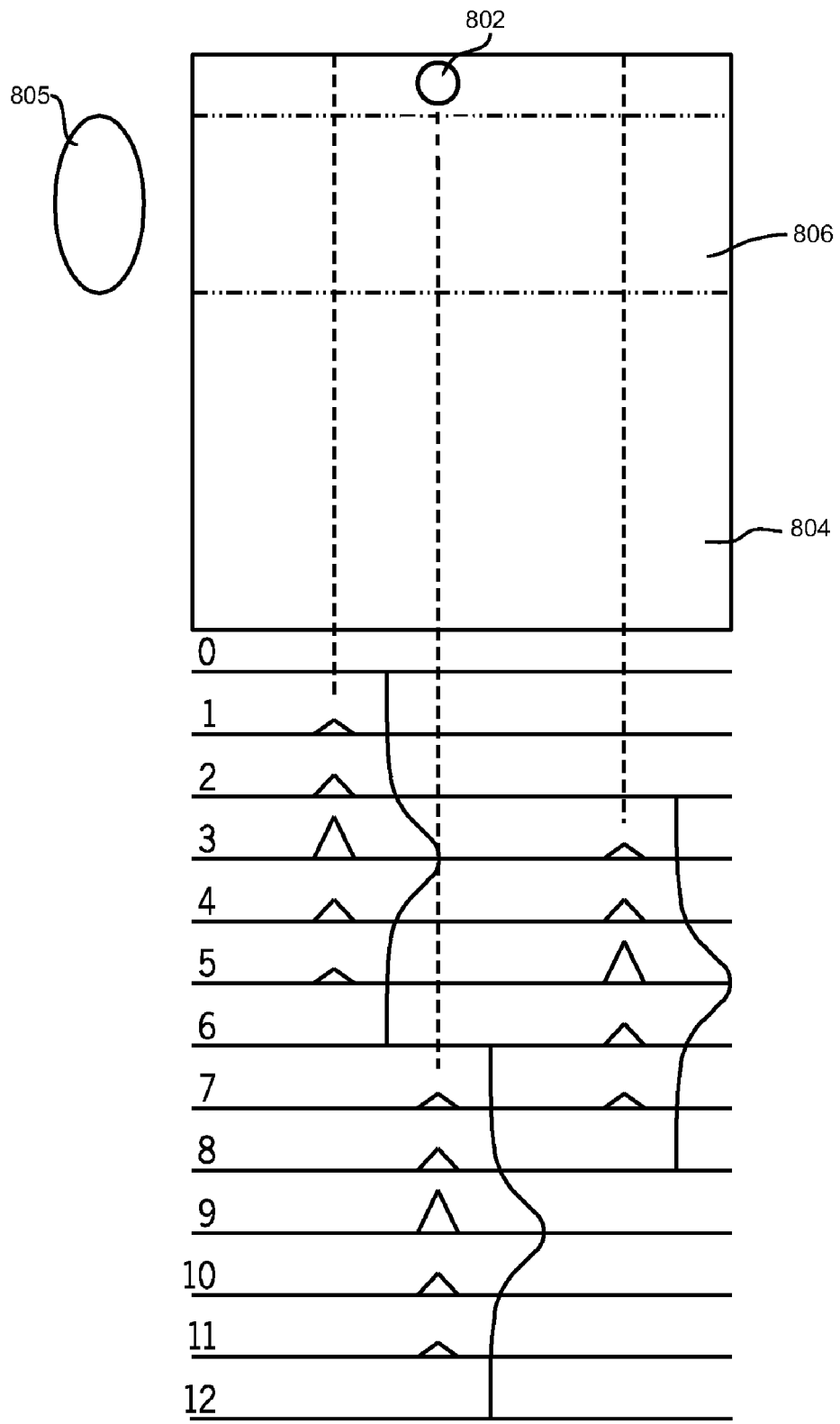

A depiction of the laser rastering method described herein, but with a plurality of cells to illustrate how the measurement rate is increased without increasing coincidences, can be seen in FIGS. 8A, 8B, 8C, 8D, 8E, 8F, 8G, 8H, 8I, 8J, 8K, 8L, and 8M. FIGS. 8A through 8M, inclusive, illustrate the movement of three cells 801, 802, and 803 moving within a sample stream 804. The cell 801 is ahead of the cell 803 by a slight distance in the sample stream 804; the cell 801 is ahead of cell 802 by a greater distance in the sample stream 804. The cells 801, 802, and 803 are moving upwardly. The cells 801, 802, and 803, which are merely just three of the cells in the sample stream 804, are illuminated by a beam of light 805, which is rastered, i.e., is swept from side to side, by a deflection device, such as, for example, an AOM. The sweeping movement of the beam describes a band 806, in sample stream 804, where cells are illuminated by the light beam at some point in the course of each raster scan. The series of horizontal lines 0 through 12, inclusive, below the sample stream 804, illustrates the sequence of varying signals (for a representative detector channel) generated by each cell at a well-defined point in each scan, or sweep. For example, at time=0 (FIG. 8A), none of the cells 801, 802, 803 have interacted with the beam 805 in the region 806. Line 0 indicates the lack of a signal peak. At time=1 (FIG. 8B), the cell 801 interacts with a low-intensity portion of the beam 805, but the cells 802 and 803 have not yet interacted with the beam 805. Line 1 indicates a low signal peak for the interaction of the beam 805 with the cell 801. At time=2 (FIG. 8C), the cell 801 interacts with a portion of the beam 805 that is intermediate to the low-intensity portion of the beam 805 and to the high-intensity portion of the beam 805, but the cells 802 and 803 have not yet interacted with the beam 805. Line 2 indicates a higher signal peak for the interaction of the cell 801 with the beam 805 than was observed at time=1 (Line 1). At time=3 (FIG. 8D), the cell 801 interacts with a high-intensity portion of the beam 805, the cell 803 interacts with a low-intensity portion of the beam 805, but the cell 802 has not yet interacted with the beam 805. Line 3 indicates the signal peaks for the interaction of the beam 805 with the cell 801 (highest signal peak for the cell 801) and with the cell 803 (low signal peak for the cell 803). At time=4 (FIG. 8E), the cell 801 interacts with a portion of the beam 805 intermediate to the high-intensity portion of the beam 805 and to the low-intensity portion of the beam 805, the cell 803 interacts with a portion of the beam 805 that is intermediate to the low-intensity portion of the beam 805 and to the high-intensity portion of the beam 805, but the cell 802 has not yet interacted with the beam 805. Line 4 indicates the signal peaks for the interaction of the beam 805 with the cell 801 (intermediate signal peak for the cell 801) and with the cell 803 (intermediate signal peak for the cell 803). Table 1 summarizes the results of the aforementioned interactions of the cells 801, 802, and 803 and the remaining interactions of the cells 801, 802, and 803 with the beam 805 across the region 806 up to the point where the cell 802 departs the region 806 of illumination by the beam 805. It should be noted that FIGS. 8A, 8B, 8C, 8D, 8E, 8F, 8G, 8H, 8I, 8J, 8K, 8L, and 8M depict schematic, not actual, interactions of the cells with the beam. In Table 1, there are four types of interactions depicted: (a) no interaction, when no part of the beam 805 intersects a cell; (b) low signal peak, when a low-intensity portion of the beam 805 intersects a cell; (c) high signal peak, when a high-intensity portion of the beam 805 intersects a cell; and (d) intermediate signal peak, when the cell intersects a portion of the beam 805 that is intermediate to the low-intensity portion of the beam 805 and to the high-intensity portion of the beam 805.

TABLE 1

| Time (FIG. no.) | Character of signal peak based on intersection of the cell 801 with the beam 805 in region 806 | Character of signal peak based on intersection of the cell 802 with the beam 805 in region 806 | Character of signal peak based on intersection of the cell 803 with the beam 805 in region 806 |
| --- | --- | --- | --- |
| 0 (8A) | none | none | none |
| 1 (8B) | low | none | none |
| 2 (8C) | intermediate | none | none |
| 3 (8D) | high | none | low |
| 4 (8E) | intermediate | none | intermediate |
| 5 (8F) | low | none | high |
| 6 (8G) | none | none | intermediate |
| 7 (8H) | none | low | low |
| 8 (8I) | none | intermediate | none |
| 9 (8J) | none | high | none |
| 10 (8K) | none | intermediate | none |
| 11 (8L) | none | low | none |
| 12 (8M) | none | none | none |

The sequence shown in FIGS. 8A through 8M, inclusive, constitutes a discrete sampling of the profile of the beam of the source of light 805. Correlation (by fit, filtering, other algorithm, or dedicated electronic circuit) of the sampled interactions with a curve representing the profile of the light beam in the vertical direction occurs in real time on all of the points, along the digitized raster scans, wherein there is a non-zero peak (such points are diagrammatically indicated by the dashed lines in FIGS. 8A through 8M, inclusive). Accordingly, each separate sequence of detected peaks belonging to a single cell can be fit to a representation of that profile. By using the technique of rastering described herein, the cells 801, 802, and 803 can be distinguished from one another, even though two or more of them may pass through the illumination region 806 simultaneously, because they interact with the beam 805 at different points of each raster scan. Accordingly, the technique of rastering enables a flow cytometer to analyze a greater number of cells per unit time, while the number of coincidences can be maintained at an acceptably low level.

The processing of the signals, from each detector, following the interactions described in FIG. 8, is depicted schematically in FIG. 9. The block diagram 900 shows a collection of detectors 902, 904, . . . (two detectors are shown as representative of an optionally larger set). Each detector is connected to a separate preamplifier circuit 912, 914, . . . (again, two preamplifier circuits are shown as representative of an optionally larger set commensurate with the number of detectors used). The preamplifier circuits for the various detectors may physically reside on the same electronic submodule, or they may be partitioned according to electrical requirements (such as, for example, noise isolation, voltage supply requirements, physical proximity to the detector, etc.) pertaining to each detector, or some portion of them may be combined and some portion kept separate. The signals from each detector so amplified by each preamplifier circuit then progress through an analog signal conditioning submodule 920. The functions of this submodule include reduction or elimination of dc offsets from each of the signals (a process also known as baseline restoration), partial or complete compensation of nonuniformities in the intensity of the light delivered to the flowcell as a function of position along the raster scan (a process also known as AOM intensity compensation), and optionally filtering to reduce or remove, for example, high-frequency noise from each of the signals. The signals in each channel so conditioned then proceed to the analog-to-digital converter (ADC) submodule 930, where each signal channel has a dedicated ADC channel clocked at high frequency and sufficient resolution. The function of the ADC submodule 930 is to convert the analog signals in each channel of detection into digitized values and discrete, but closely spaced, time intervals, as shown, for example, in FIG. 6F. The signals so digitized then progress to the digital signal processing (DSP) submodule 940. This submodule 940 can comprise a single powerful field-programmable gate array (FPGA) 942, optionally a DSP chip 944, a plurality of either FPGAs or DSPs, or both an FPGA and a DSP, or a plurality of FPGAs and DSPs, depending on the speed and computational requirements of the specific application of the analyzer in which they are incorporated. Additionally, submodule 940 preferably embodies: (a) random access memory (RAM) units 946 for intermediate storage of data for computation, for staging data before transmission over a data bus or other means of conveyance to the next stages of processing, or for both intermediate and staging data storage; and (b) a digital-to-analog converter (DAC) unit 948 that takes inputs from the FPGA(s) 942, the DSP(s) 944, or both the FPGA(s) 942 and the DSP(s) 944 and converts them into analog signals. These analog signals are used to dynamically, or programmatically, alter the operating parameters (e.g., supply voltage) of portions or a totality of the detectors 902, 904, . . . ; the operating parameters (e.g., gain settings) of the preamplifier submodules 912, 914, . . . ; the operating parameters (e.g., amount of dc offset) of the analog submodule 920; or a combination of operating parameters of detectors, preamplifiers, and analog submodule. The functions of the DSP submodule 940 are to: (a) select the highest digitization value from a cell interaction during a single raster scan (or a plurality of such values, if more than a single cell is present during a single raster scan as shown, for example, in FIG. 8E); (b) to optionally apply a known factor to the values thus identified, based on their position along the raster scan, in order to effect any necessary residual AOM intensity compensation not already executed in the analog submodule 920; (c) to correlate such highest values across successive raster scans in order to reconstruct the peak value of the interaction between each cell and the light beam spot (as illustrated, for example, in FIGS. 7D and 8A through 8M); (d) to apply programmatically predetermined numerical upper, lower, or upper and lower, thresholds, specific to each channel of detection, to the peak values so reconstructed in order to select out of the population of detected events those that, within a particular assay, are most likely to represent the population of interest, and to reject or differently classify the remainder; and (e) to coordinate the information thus constructed and filtered, coming from each individual channel of detection, into a digital entity (typically referred to as one element of a "listmode" file) that contains time-stamp information as well as the reconstructed value from each of the channels of detection involved in the measurement pertaining to that same individual detection event. The collection of listmode events is then collated into one or a plurality of listmode batches, which are temporarily stored, e.g., in RAM units 946. The batches of data are then periodically transferred, at programmatically determined times, to the analyzer operating system (AOS) 950 for further processing by algorithms, such as, for example, cell identification and counting.

The present invention provides an instrument that maintains satisfactory performance with respect to precision, coincidences, and signal-to-noise ratio. The method of the present invention allows selection of rastering speeds to conform to the desired digitization frequency and to allow multiple scans over a single cell. The present invention can be implemented with commercially available components (e.g., AOM, ADC, FPGA). The present invention can provide a substantial improvement in the measurement rate (cells analyzed per second). This improvement results in: (a) a reduction in the time required to perform a standard CBC, thereby yielding a higher throughput (CBC/hr); (b) an increase in the total number of cells analyzed per sample run, thereby yielding higher statistical precision in the determination of, in particular, the existence, the concentration, or the existence and the concentration of relatively rare cellular events; or (c) a combination of both a higher throughput and an increase in the number of total cells analyzed.

The conditional constraints of the present invention are summarized by the following mathematical relationships, where the parameters represented by primed symbols indicate the parameter values in the invention described herein, and the parameters represented by unprimed symbols indicate the parameter values in the prior art:

1(signal strength): $\dfrac{P'_{laser}}{w'_{ox} w'_{oy}} \geq \dfrac{P_{laser}}{w_{ox} w_{oy}}$

2(coincidences): $w'_{ox} w'_{oy} z'_{stream} \leq x_{stream} w_{oy} z_{stream}$

3(multiple digitizations over cell): $\dfrac{w'_{ox} f'_{digitization}}{x'_{stream} f_{raster}} \geq 10$

4(digitization limit): $f'_{digitization} \leq 125$ MHz

5(multiple raster scans over cells): $\dfrac{w'_{oy} f'_{raster}}{v'_{stream}} \geq 3$

6(rastering limit): $f'_{raster} \leq 1$ MHz

7(measurement rate requirement):

$$x'_{stream} z'_{stream} v'_{stream} \geq x_{stream} z_{stream} v_{stream}$$

where $P_{laser}$ represents the laser beam power,
$w_{ox}$ and $w_{oy}$ represent the dimensions of a focused spot (i.e., at or near the waist) of a laser beam (horizontal and vertical, respectively),
$x_{stream}$ and $z_{stream}$ represent the dimensions of the sample stream (width and depth, respectively),
$v_{stream}$ represents the velocity of the sample stream,
$f_{digitization}$ represents the digitization frequency,
$f_{raster}$ represents the frequency of repetition of the raster scans.

As used herein, the phrase "conditional constraint" means a value expressed as a mathematical relationship for establishing target operating conditions for a flow cytometry apparatus and method. It is understood that such constraints are only broadly indicative of the ultimate operating conditions selected for implementation, such as, for example, constraints attributable to technological limitations, such as the speed of electronic components, which can be relaxed by the introduction of improved devices. Also, other constraints may represent the absolute minimum requirement for a particular operating parameter, wherein good engineering design considerations would suggest adoption of a value of such a parameter with a margin of tolerance for manufacturing, operating, and specimen variabilities. Implicit in these conditions are the assumptions that in like assays, the dilution levels remain unchanged.

Turning to the signal strength parameter, condition #1 (signal strength) is defined by the following relationship:

$$\dfrac{P'_{laser}}{w'_{ox} w'_{oy}} \geq \dfrac{P_{laser}}{w_{ox} w_{oy}} \qquad \text{condition \#1}$$

Figure 11:
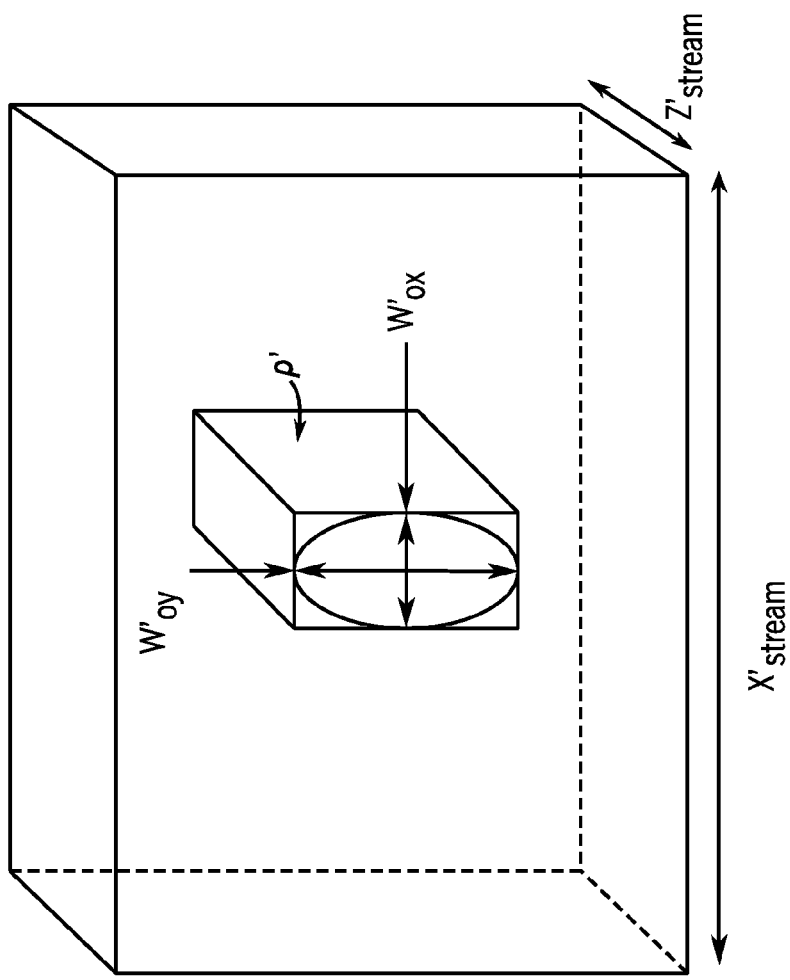
FIG. 11 is the analogue of FIG. 10 for the present invention.
Figure 10:
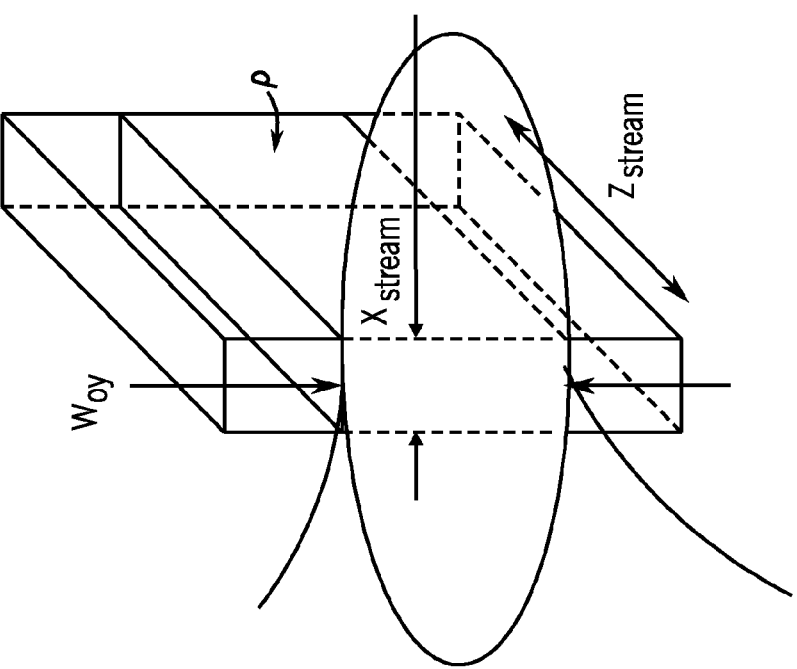
FIG. 10 is a schematic diagram of a volume of sample illuminated at any one time by a laser beam of the prior art.

Turning now to the coincidences parameter, FIG. 10 shows diagrammatically an illuminated volume of the prior art, and FIG. 11 shows diagrammatically an illuminated volume encountered in the present invention. The following two relationships provide the parameters utilized to determine the number of cells in the volume illuminated at any instant of time. The term "current" refers to the prior art. The term "new" refers to the present invention.

$N_{cells} = \rho x_{stream} w_{oy} z_{stream}$ current number of cells in illuminated volume $N'_{cells} = \rho' w'_{ox} w'_{oy} z'_{stream}$ new number of cells in illuminated volume With the assumption that, in like assays, the dilution levels in the present invention ($\rho'$) are unchanged from their values in the prior art ($\rho$), condition #2 (coincidences) can be defined by the following relationship:

$$w'_{ox} w'_{oy} z'_{stream} \leq x_{stream} w_{oy} z_{stream} \qquad \text{condition \#2}$$

It is also understood that altering the dilution levels in an assay is possible and may be warranted under certain circumstances, and that this would modify condition #2 accordingly.

Figure 12A:
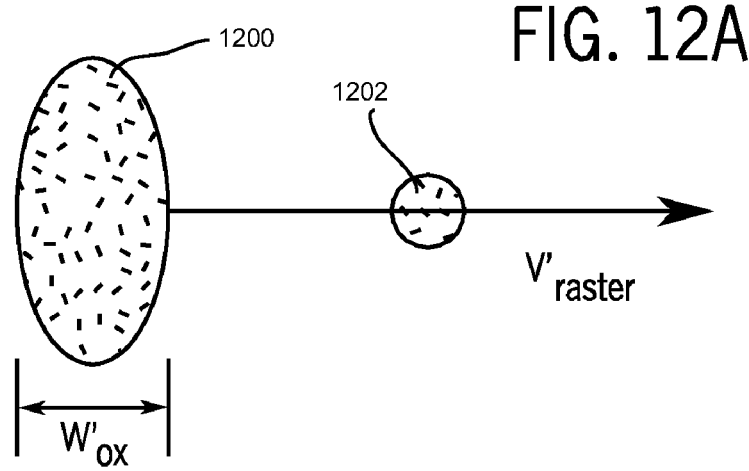
FIGS. 12A, 12B, and 12C are schematic diagrams illustrating the laser beam interacting with a cell.
Figure 12B:
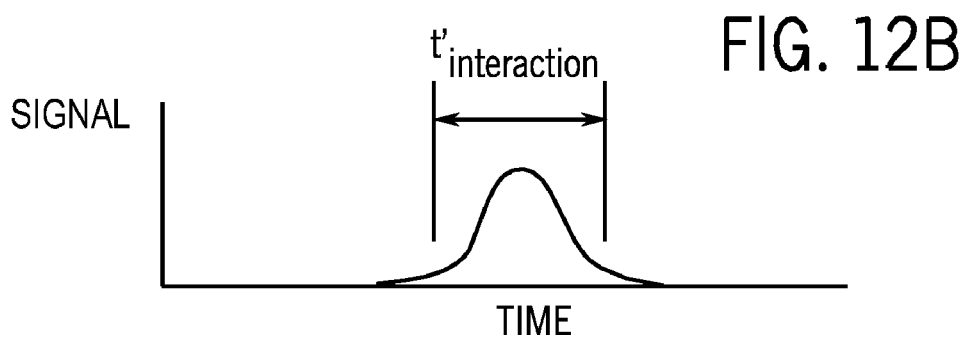
Figure 12C:
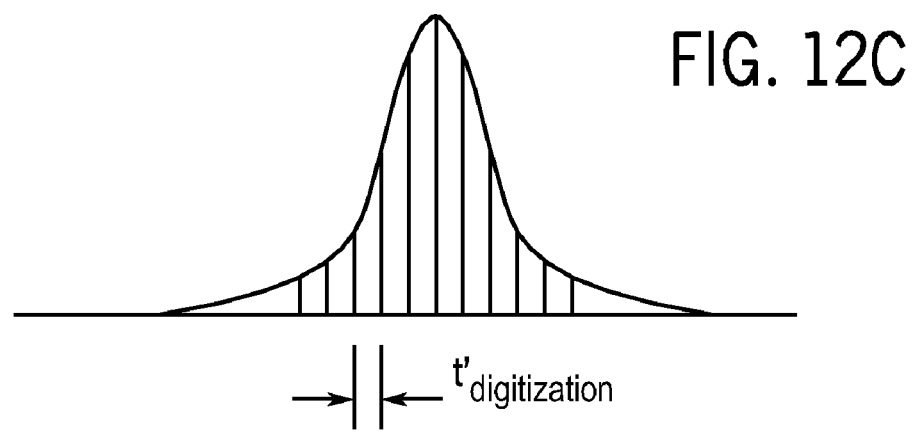

Turning now to the digitizations parameter, FIG. 12A shows diagrammatically the dimensions of a laser beam spot 1200. FIG. 12B shows a hypothetical plot of signal intensity as a function of time. FIG. 12C shows a hypothetical plot of digitizations developed by an analog-to-digital converter. Based on the following relationships, i.e.:

$$t'_{interaction} = \dfrac{w'_{ox}}{v'_{raster}} \qquad \text{interaction time}$$

$$= \dfrac{w'_{ox}}{x'_{stream} f'_{raster}}$$

$$t'_{digitization} = \dfrac{1}{f'_{digitization}} \qquad \text{digitization time}$$

condition #3 (multiple digitizations over cell) can be defined by the following relationship:

$$\dfrac{w'_{ox} f'_{digitization}}{x'_{stream} f'_{raster}} \geq 10 \qquad \text{condition \#3}$$

where the number 10 is selected to indicate the approximate number of digitizations required to capture with sufficient accuracy the varying profile of the signal from interaction between the laser beam and a cell in the course of a raster scan.

For condition #4 (digitization limit), the mechanism of ADCs is such that a trade-off relationship exists between the digitization frequency and the depth of resolution. The fastest commercially available analog-to-digital converters can digitize with 14-bit resolution at 125 MHz or with 16-bit resolution at 100 MHz. For the purpose of the current invention, a 14-bit resolution is adequate, while the highest possible frequency of digitization is desired. Therefore, condition #4

$$f_{digitization} \leq 125 \text{ MHz} \qquad \text{condition \#4}$$

where the condition is meant to indicate the constraint imposed by the performance of currently available technology, and not the maximum digitization frequency desired in principle for the purpose of this invention.

Figure 13:
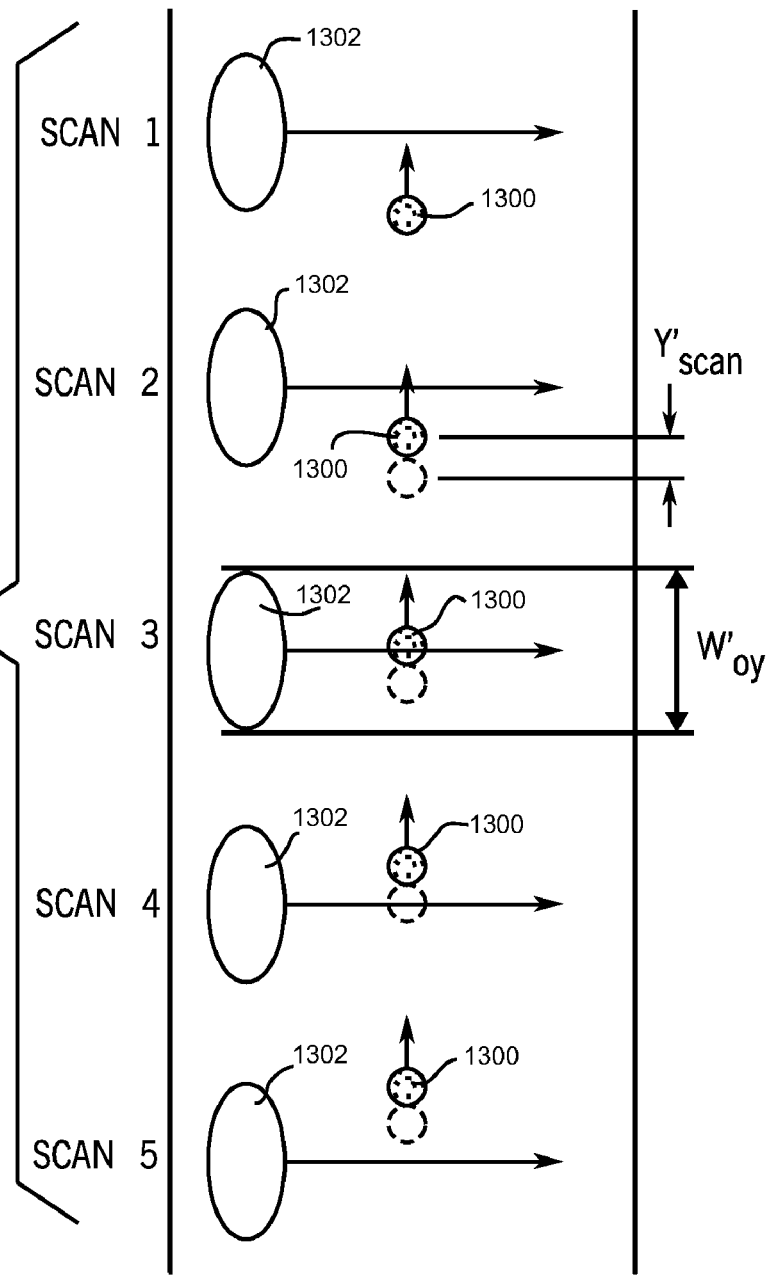
FIG. 13 is a schematic diagram illustrating the laser beam interacting repeatedly with a cell in the course of five consecutive raster scans.

Turning now to the multiple raster scans parameter, hypothetical scans 1, 2, 3, 4, and 5 of FIG. 13 diagrammatically show the position of a cell 1300 during each of a plurality of scans of the laser beam 1302. Here $y'_{scan}$ represents the distance advanced by a cell during one scan, and $w'_{oy}$ represents the beam spot size along the major (vertical) axis of the elliptical beam. Based on the following relationships, i.e.:

$$t'_{raster} = \dfrac{1}{f'_{raster}} \qquad \text{raster period}$$

$$y'_{scan} = v'_{stream} t'_{raster} \qquad \text{distance advanced in one scan}$$

$$= \dfrac{v'_{stream}}{f'_{raster}}$$

$$w'_{oy} \qquad \text{vertical beam spot size}$$

condition #5 (multiple raster scans over cell) can be defined by the following relationship:

$$\dfrac{w'_{oy} f'_{raster}}{v'_{stream}} \geq 3 \qquad \text{condition \#5}$$

where the number 3 is selected to indicate the minimum number of scans required to allow, in principle, a reconstruction of the Gaussian curve representing the interaction between the laser beam and a cell in the course of multiple raster scans.

For condition #6 (rastering limit), the mechanism of AOMs is such that a trade-off relationship exists between the range of deflection angles and the frequency of rastering. For the purpose of the current invention, the range of deflection angles can be relatively small, while the highest possible frequency of rastering is desired. Commercially available AOMs optimized for this purpose can effect sweeps over approximately 1 to 2 mrad at a maximum repetition frequency of approximately 1 MHz. Therefore, $$f_{raster} \leq 1 \text{ MHz} \qquad \text{condition \#6}$$

where the condition is meant to indicate the constraint imposed by the performance of currently available technology, and not the maximum rastering frequency desired in principle for the purpose of this invention.

Figure 15:
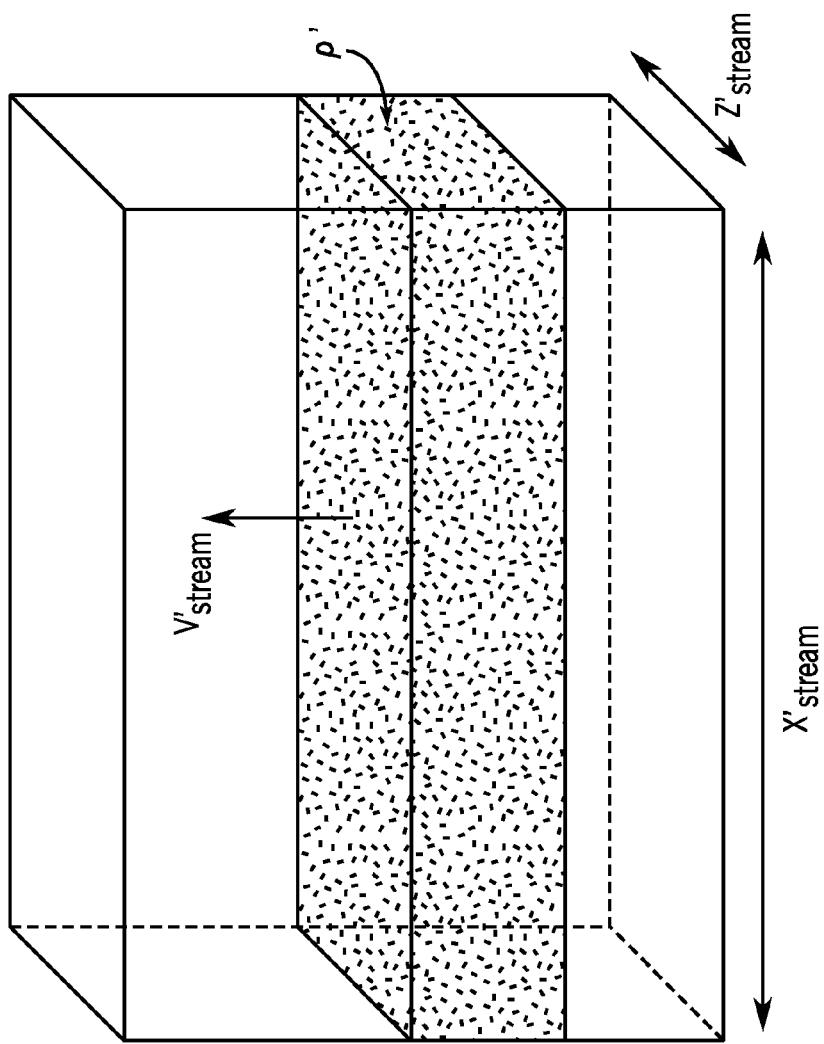
FIG. 15 is the analogue of FIG. 14 for the present invention.
Figure 14:
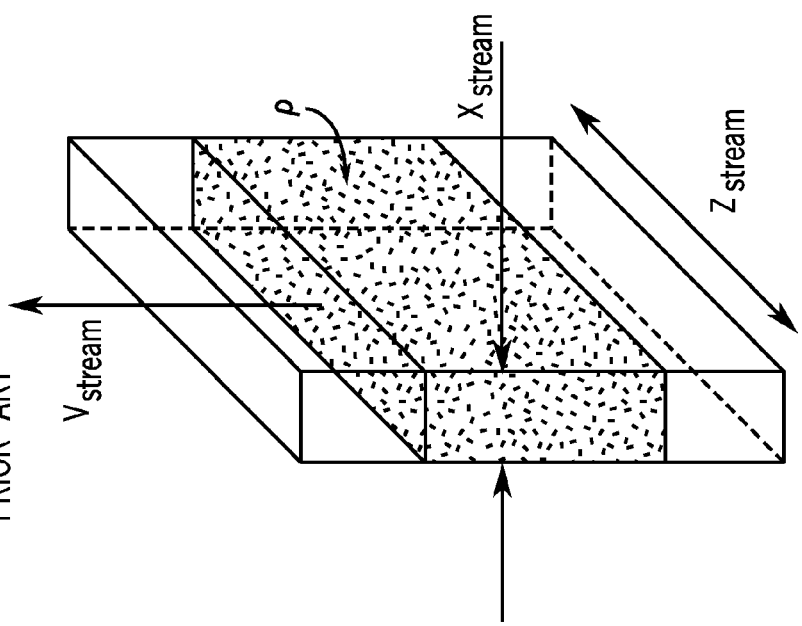
FIG. 14 is a schematic diagram of a volume of sample interrogated by a laser beam in a given unit of time in the prior art.

Turning now to the measurement rate parameter, FIG. 14 shows diagrammatically a volume of sample of the prior art measured in a given unit of time and FIG. 15 shows diagrammatically a volume of sample measured in the same unit of time in the present invention. It is important to differentiate between the volume just described (which can be substantially larger in the present invention than in the prior art) and the volume illuminated by the laser beam at any one instant of time, depicted instead in FIGS. 10 and 11 for the prior art and the present invention, respectively (where such illuminated volume is intended to be essentially equivalent in the present invention and in the prior art). The reason for the difference is that in the prior art the volume measured per unit time depends mainly on the illuminated volume and on the stream velocity, whereas in the present invention the volume measured per unit time is augmented by the rastering process to include multiples of the illuminated volume. The following two relationships provide parameters to determine the measurement rate (defined as the number of cells detected per unit time), where the term "current" refers to the prior art and the term "new" refers to the present invention:

$n = \rho x_{stream} z_{stream} v_{stream}$ current measurement rate (cells/sec)

$n' = \rho' x'_{stream} z'_{stream} v'_{stream}$ new measurement rate (cells/sec)

Condition #7 (measurement rate requirement) is defined by the following relationship:

$$x'_{stream} z'_{stream} v'_{stream} \leq x_{stream} z_{stream} v_{stream} \qquad \text{condition \#7}$$

The foregoing relationships allow one to select choices for each parameter and verify that each condition is satisfied, and by what margin. The following set of choices represents an embodiment suitable for use in this invention:

$P'_{laser} = 10$ mW
$w'_{ox} = 10$ μm
$w'_{oy} = 20$ μm
$x'_{stream} = 100$ μm
$z'_{stream} = 40$ μm
$v'_{stream} = 4$ m/s
$f'_{raster} = 1$ MHz
$f'_{digitization} = 100$ MHz The foregoing values are contrasted, for example, with the approximate values currently employed in the CELL-DYN® Sapphire® hematology analyzer:

$P_{laser} = 10$ mW
$w_{ox} = 65$ μm
$w_{oy} = 20$ μm
$x_{stream} = 5$ μm
$z_{stream} = 80$ μm
$v_{stream} = 8$ m/s Through appropriate choices of parameters, all of the conditions previously described can be satisfied, and some can be satisfied by a significant margin. Most importantly, the condition #7 yields the dramatic result of a five-fold improvement in measurement rate with respect to what is currently achieved on the CELL-DYN® Sapphire® instrument. It is understood that this level of improvement in measurement rate is indicative of a value that can be substantially increased, within the scope of the present invention, by judicious engineering choices or by improvement of performance of utilized components. It is also understood that the foregoing choices for parameter values for the present invention are tolerant of significant variation without an attendant significant reduction in the value of the invention. For example, the rastering frequency can be reduced by some amount or the sample stream dimensions can be altered in order to satisfy engineering design requirements, while still providing the present invention with a substantial advantage in terms of measurement rate, relative to the prior art.

This invention can be used with any product line that employs a laser for carrying out flow cytometry or flow-cytometer-based hematology analysis. Instruments that are suitable for use with this invention include, but are not limited to, the CELL-DYN® Sapphire® (commercially available from Abbott Laboratories) and the CELL-DYN® Ruby® (commercially available from Abbott Laboratories). Although the nature and degree of the throughput bottlenecks in certain systems could limit some aspects of the effectiveness of this invention, a preferred implementation would involve a system where the improvement could be carried out with limited changes, but with potentially significant performance benefits. Such an implementation would solve the effective throughput problem previously described.

One benefit of this invention is a dramatic increase in the measurement rate (cells analyzed per second), such as, for example, by an approximate factor of five. This increase allows (a) a reduction in the time for acquisition of data (time for counting cells for each assay) by the same factor, thereby increasing the throughput; or (b) an increase in the total counts (total number of cells counted for each assay) by the same factor, thereby increasing precision. An increase in precision is particularly important in cytopenic patients. A combination of increases in both precision and throughput is also feasible. The specific effect on actual throughput (CBC/hr) can be estimated by assuming that only the count times are reduced by a factor of five, the remaining steps of the process being unchanged. This assumption would result in reducing the processing cycle time of the flow cell to approximately 22 seconds (flow cytometry apparatus); at this level, other bottlenecks begin to dominate, such as, for example, the white blood cell solution incubation cycle time of 24 seconds for lysing the red blood cells. So, without having to adjust the lyse reagents and reaction conditions, one can envision simply matching this bottleneck and achieving 150 CBC/hr. Introducing relatively minor additional changes into the analyzer, such as a reduced incubation time at higher temperature, or an additional lysing chamber for parallel processing of samples, would remove the incubation bottleneck and allow further improvements in the effective throughput of the analyzer. It is important to note that the relevant parameter in a clinical application is the overall effective throughput of an analyzer, which includes not only the mechanical throughput performance (in terms of CBC/hr), but also the rate of first-pass reportability of the results. An instrument such as the CELL-DYN® Sapphire®, already noted for its excellent first-pass reportability performance, would greatly benefit from such a dramatic increase in mechanical throughput. An application aimed at maximizing precision performance would not be sensitive to the incubation bottleneck and could derive significant benefit from the present invention.

An attendant benefit of the present invention in a hematology analyzer or flow cytometer is the ability to independently determine multiple parameters closely correlated with the size of the particle(s) being subjected to measurement. Determining the size of cells in the sample is one of the principal functions of a hematology analyzer. In the prior art of flow-cytometer-based instrumentation, cell size determination is typically achieved by processing the signal from one or more of the scattering detectors, particularly the forward-scattering ones. This same capability is available, unchanged, in the present invention. Another approach taken in the prior art has been to measure the so-called "time of flight," namely the time it takes a particle to traverse the stationary laser light beam spot. Referring to FIG. 5, i.e., the prior art, time of flight would be approximately represented by the width of the interaction signal curve 506. (This is actually a correlation of the size of the particle and the width of the laser beam spot; if the laser beam spot size is known, the particle size can be determined.) In the present invention, there are multiple opportunities for obtaining a time-of-flight measurement of the size of the cell under scrutiny. First, each raster scan that interacts with a cell can optionally return a value for the width of such interaction. Referring to FIGS. 7A, 7B, and 7C, the width of each of the interaction curves represents an independent measurement of the size of the cell 702. The availability of a multiplicity of such determinations provides a statistical robustness of precision to the collection of size values that is unmatched by a single determination as is used in the prior art. Second, referring to FIG. 7D, the correlation across raster scans that yields the peak value of the interaction can likewise yield the width of such interaction. This determination represents an additional measurement of the size of the cell, which can be combined and correlated with the determinations from each raster scan to result in a robust collection of size-related measurements independent of, and augmenting, those derived from the scattering information itself.

The method of this invention can be utilized in various environments through the use of a modular approach. A very fast version (leveraging the aspect of the invention related to the reduction in the time required for a CBC) can be used for high-volume applications in reference laboratories and hospital core laboratories, optimized for effective throughput, and possibly without monoclonal antibody features. A very precise version (leveraging the aspect of the invention related to the increase in total number of counted cells in a given unit of time) can be aimed at tertiary-care centers, optimized for performance on rare events and cytopenic samples, and including monoclonal antibody features.

The reagents used in the assays remain unchanged. None of the reagents, and none of the dilutions, are affected in the rastering scheme described herein. The cell counting and identification algorithms are unchanged. Furthermore, the algorithms employ the same data (signals) that are currently employed. The precision of results can be automatically maintained by design. The coincidence levels can be maintained by design. Problems caused by misalignment of laser beam and sample stream on account of temperature fluctuations can be eliminated. The beam "self-registers" to the sample stream with each rastering cycle, rendering slow drifts inconsequential. The entire extent of the laser beam is used, as opposed to just the small central portion of it, resulting in greater efficiency for a given power level. In the prior art, 90-95% of the beam is wasted. The stream velocity is reduced, thereby causing the system to move away from the turbulence threshold, with reduced risk for hydrodynamic instabilities.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. An apparatus for determining multi-parameter data from particles in a sample, said apparatus comprising:
    (a) a source of light;
    (b) a flow cell containing a moving sample stream, whereby particles in the sample move with the sample stream;
    (c) at least one optical element for focusing light from the source of light onto the particulate material moving with the sample stream in the flow cell;
    (d) a scanning device for deflecting the focused light from the source of light to enable the focused light to sweep back-and-forth across the moving sample stream; and
    (e) at least one detector channel, said at least one detector channel including a detector, an analog-to-digital converter, and a digital signal processing module,
    wherein a horizontal dimension of the focused light is ten times or more greater than a width dimension of the sample stream, multiplied by a scanning frequency of the scanning device, divided by a frequency of digitization of the digital signal processing module, and
    wherein a vertical dimension of the focused light is three times or more greater than a velocity of the sample stream through the flow cell, divided by the scanning frequency of the scanning device.

2. The apparatus of claim 1, wherein said flow cell has cross-sectional dimensions sufficient to enable the formation of a sample stream in which a plurality of particles can flow along side of one another.

3. The apparatus of claim 1, wherein said scanning device is an acousto-optic modulator.

4. The apparatus of claim 1, wherein said digital signal processing module comprises a field-programmable gate array.

5. The apparatus of claim 4, wherein said digital signal processing module comprises sufficient on-board memory registers to hold intermediate values for computation and a digital-to-analog converter.

6. The apparatus of claim 1, wherein said at least one detector channel further comprises an analog signal conditioning submodule.

7. The apparatus of claim 1, wherein said digital signal processing module comprises a digital signal processing chip.

8. The apparatus of claim 1, wherein said at least one detector channel further comprises a preamplifier circuit.

9. A method for generating multi-parameter data from particles, said method comprising the steps of:
    (a) providing an optical module comprising a source of light, a flow cell containing a moving sample stream, whereby particles in the sample move with the sample stream; at least one optical element for focusing light from the source of light onto the particulate material moving with the sample stream in the flow cell; a scanning device for deflecting the focused light from the source of light to enable the focused light to sweep back-and-forth across the moving sample stream; and at least one detector channel, said at least one detector channel including a detector, an analog-to-digital converter and a digital signal processing module,
wherein a horizontal dimension of the focused light is ten times or more greater than a width dimension of the sample stream, multiplied by a scanning frequency of the scanning device, divided by a frequency of digitization of the digital signal processing module, and
wherein a vertical dimension of the focused light is three times or more greater than a velocity of the sample stream through the flow cell, divided by the scanning frequency of the scanning device;
(b) providing an electronic module capable of digitizing signals obtained from said optical module;
(c) using the optical module to interrogate particles flowing in a sample stream through the flow cell to obtain data relating to the particles; and
(d) determining parameters from the data obtained by interrogating the particles.

10. The method of claim 9, wherein said determination of parameters is carried out by means of time-of-flight measurements.

11. The method of claim 9, wherein said scanning device is an acousto-optic modulator.

12. The method of claim 9, wherein said digital signal processing module comprises a field-programmable gate array.

13. The method of claim 12, wherein said digital signal processing module comprises sufficient on-board memory registers to hold intermediate values for computation and a digital-to-analog converter.

14. The method of claim 9, further including the step of providing an analog signal conditioning submodule to said at least one detector channel.

15. The method of claim 9, wherein said digital signal processing module comprises a digital signal processing chip.

16. The method of claim 9, further including the step of providing a preamplifier circuit to said at least one detector channel.

17. The apparatus of claim 1, wherein the digitization frequency of the digital signal processing module is less than or equal to 125 MHz.

18. The apparatus of claim 1, wherein the scanning frequency is less than or equal to 1 MHz.

19. The method of claim 9, wherein the data is digitized at a frequency of less than or equal to 125 MHz.

20. The method of claim 9, wherein the light is swept at a frequency less than or equal to 1 MHz.

* * * * *